United States Patent [19]

Revankar et al.

[11] Patent Number: 5,446,045
[45] Date of Patent: Aug. 29, 1995

[54] ANTIVIRAL GUANINE ANALOGS

[76] Inventors: Ganapathi R. Revankar, 180 N. Milltrace Dr., The Woodlands, Tex. 77381; Arthur F. Lewis, 2301 Millbend Dr. #2412, The Woodlands, Tex. 77380; Birendra K. Bhattacharya, 58 E. Stony End Pl., The Woodlands, Tex. 77381; Rodrigo V. Devivar, 26001 Budde Rd., #2003, Spring, Tex. 77380; Robert F. Rando, 35 Dovetail Pl., The Woodlands, Tex. 77381; Susan M. Fennewald, 2500 Tanglebrush #187, The Woodlands, Tex. 77381

[21] Appl. No.: 170,559

[22] Filed: Dec. 20, 1993

[51] Int. Cl.6 .......................... A61K 31/505
[52] U.S. Cl. ...................... 514/258; 514/45; 514/266; 514/300; 514/301; 514/302; 514/81; 536/27.14; 536/27.61; 536/27.62; 536/27.63; 536/27.7; 536/27.8; 536/27.81; 544/258; 544/244; 546/113; 546/114; 546/116; 546/23
[58] Field of Search .............. 544/255; 514/258

[56] References Cited

U.S. PATENT DOCUMENTS

| | | | |
|---|---|---|---|
| 4,746,651 | 5/1988 | Goodman | 514/45 |
| 4,880,784 | 11/1989 | Robins et al. | 514/48 |
| 5,166,141 | 11/1992 | Goodman et al. | 514/45 |

FOREIGN PATENT DOCUMENTS

0531597A1  3/1993  European Pat. Off.

OTHER PUBLICATIONS

Bhattacharya et al. Chem. Abstr. vol. 121 entry 8983 (1994).

W. Ashton, et al., "Synthesis and Antiherpetic Activity of (±)-9-[[(Z)-2-(hydroxymethyl)cyclopropyl]methyl]guanine and Related Compounds" *J. Med. Chem.* 31:2304–2315 (1988).

E. Badawey, et al., "Potential anti-microbials, I. Synthesis and structure-activity studies of some new thiazolo[4,5-d]pyrimidine derivatives" *Eur. J. Med. Chem.* 28:91–96 (1993).

E. Badawey, et al., "Potential anti-microbials. II. Synthesis and in vitro anti-microbial evaluation of some thiazolo[4,5-d]pyrimidines" *Eur. J. Med. Chem.* 28:97–101 (1993).

J. Baker, et al., "Synthesis of Derivatives of Thiazolo[4,5-d]pyrimidine, Part I." *J. Chem. Soc.* pp. 603–606 (1969).

J. Baker, et al., "Synthesis of Derivatives of Thiazolo[4,5-d]pyrimidine, Part II." *J. Chem. Soc.* pp. 2478–2484 (1970).

B. Bhattacharya, et al., "Synthesis of Certain N- and C-Alkyl Purine Analogs." *J. Het. Chem.* vol. 30, No. 5 pp. 1341–1349 (Oct.–Nov. 1993).

(List continued on next page.)

*Primary Examiner*—Donald G. Daus
*Attorney, Agent, or Firm*—Fulbright & Jaworski

[57] ABSTRACT

A series of guanine analogs having the basic structures of

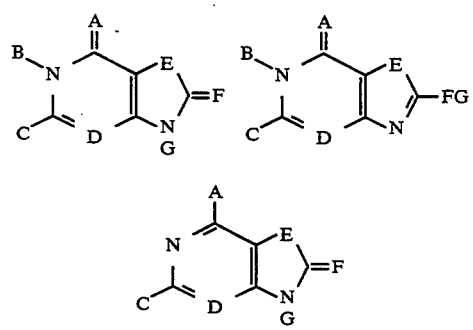

and physiological salts thereof. Also disclosed are a variety of the use of the compounds as a composition with a physiological carrier or in combination therapy with acyclovir, HBG and ganciclovir in the treatment of viral disease.

4 Claims, 3 Drawing Sheets

HCMV Plaque Reduction in HFF Cells

OTHER PUBLICATIONS

P. Bonnet, et al., "Modulation of Leukocyte Genetic Expression by Novel Purine Nucleoside Analogues. A New Approach to Antitumor and Antiviral Agents" *Journal of Medicinal Chemistry* 36:635–653 (1993).

D. Borcherding, "Potential Inhibitors of S–Adenosylmethionine–Dependent Methyltransferases. II. Molecular Dissections of Neplanocin A as Potential Inhibitors of S–Adenosylhomocysteine Hydrolase" *J. Med. Chem.* 31:1729–1738 (1988).

C. Chu, et al., "Chemistry and Antiviral Activities of Acyclonucleosides" *J. Heterocyclic Chem.* 23:289–319 (1986).

J. Colacino, et al., "Antiviral Activity of 2'-2'-Fluoro-β-D-Arabinofuranosyl-5-Iodocytosine Against Human Cytomegalovirus in Human Skin Fibroblasts" *Antimicrobial Agents and Chemotherapy* 28:252–258 (1985).

D. Haines, et al., "Synthesis and Biological Activity of Unsaturated Carboacyclic Purine Nucleoside Analogues" *J. Med. Chem.* 30:943–947 (1987).

M. Harnden, et al., "Novel Acyclonucleotides: Synthesis and Antiviral Activity of Alkenylphosphonic Acid Derivatives of Purines and a Pyrimidine" *J. Med. Chem.* 36:1343–1355 (1993).

S. Hayashi, et al., "Adenallene and cytallene: Acyclic nucleoside analogues that inhibit replication and cytopathic effect of human immunodeficiency virus in vitro" *Proc. Natl. Acad. Sci. USA* 85:6127–6131 (1988).

P. Herdewijn, "Novel nucleoside strategies for anti-HIV and anti-HSV therapy" *Antiviral Research* 19:1–14 (1992).

A. Katritzky, et al., "The Preparation of Symmetrical Secondary Alkyl Bromides" *Chemica Scripta* 27:477–478 (1987).

G. Kini, et al., "Synthesis and Antiviral Activity of Certain Guanosine Analogues in the Thiazolo[4,5-d]-pyrimidine Ring System" *J. Med. Chem.* 34:3006–3010 (1991).

A. Larsson, et al., "Mode of Action, Toxicity, Pharmacokinetics, and Efficacy of Some New Antiherpesvirus Guanosine Analogs Related to Buciclovir" *Antimicrobial Agents and Chemotherapy* 30:598–605 (1986).

C. Lopez, et al., "2'-Fluoro-5-Iodo-Aracytosine, a Potent and Selective Anti-Herpesvirus Agent" *Antimicrobial Agents and Chemotherapy* 17:803–806 (1980).

S. Megati, et al., "Unsaturated Phosphonates as Acyclic Nucleotide Analogues. Anomalous Michaelis–Arbuzov and Michaelis–Becker Reactions with Multiple Bond Systems" *J. Org. Chem.* 57:2320–2327 (1992).

M. Michael, et al., "Alkylpurines as Immunepotentiating Agents. Synthesis and Antiviral Activity of Certain Alkylguanines" *J. Med. Chem.* 36:3421–3436 (1993).

K. Nagahara, et al., "Thiazolo[4,5-d]prymidine Nucleosides. The Synthesis of Certain 3-β-D-Ribofuranosylthiazolo[4,5-d]pyrimidines as Potential Immunotherapeutic Agents" *J. Med. Chem.* 33:407–415 (1990).

S. Phadtare, et al., "Nucleic Acid Derived Allenols: Unusual Analogues of Nucleosides and Antiretroviral Activity" *J. Am. Chem. Soc.* 111:5925–5931 (1989).

S. Phadtare, et al., "Synthesis and Biological Properties of 9-(trans-4-Hydroxy-2-buten-1-yl)adenine and Guanine: Open-Chain Analogues of Neplanocin A" *J. Med. Chem.* 30:437–440 (1987).

S. Phadtare, et al., "Unsaturated and Carbocyclic Nucleoside Analogues: Synthesis, Antitumor, and Antiviral Activity" *J. Med. Chem.* 34:421–429 (1991).

M. Robins, et al., "Nucleic acid related compounds. 37. Convenient and high-yield syntheses of N-[2-hydroxyethoxy)methyl]heterocycles as acrylic nucleoside analogues" *Can. J. Chem.* 60:547–553 (1982).

C. Tann, et al., "Fluorocarbohydrates in Synthesis. An Efficient Synthesis of 1-(2-Deoxy-2-fluoro-β-D-arabinofuranosyl)-5-iodouracil (β-FIAU) and 1-(2-Deoxy-2-fluoro-β-D-arabinofuranosyl)thymine (β-FMAU)" *J. Org. Chem.* 50:3644–3647 (1985).

I. Verheggen, et al., "Synthesis and Antiherpes Virus Activity of 1,5-Anhydrohexitol Nucleosides" *J. Med. Chem.* 36:2033–2040 (1993).

K. Watanabe, et al., "Nucleosides. 110. Synthesis and Antiherpes Virus Activity of Some 2'-Fluoro-2'-deoxyarabinofuranosylpyrimidine Nucleosides" *Journal of Medicinal Chemistry* 22:21–24 (1979).

ANTIVIRAL GUANINE ANALOGS

FIELD OF THE INVENTION

The present invention relates generally to guanine analogs which can be useful as antiviral agents. More particularly it relates to cyclic, acyclic and glycosyl derivatives of substituted heterocyclic ring systems and specified deaza analogs of these ring systems.

BACKGROUND OF THE INVENTION

The past two decades has seen the emergence of acyclic derivatives of guanine as drugs of choice for the treatment of certain viral caused conditions. The three most recognized of these acyclic derivatives are acyclovir [9-(2-hydroxyethoxymethyl)guanine], HBG [9-(4-hydroxybutyl)guanine], and ganciclovir [9-( 1-hydroxymethyl-2-hydroxyethoxymethyl)guanine]. Acyclovir is the current drug of choice for the treatment of herpes simplex virus (HSV) infections; whereas, ganciclovir is the standard against which other drugs are measured for their effect against human cytomegalovirus (HCMV). The diversity of like structures which have been synthesized and evaluated for their antiviral efficacy has been the subject of recent review articles[1,2]. These structures are related to each other in two ways: (1) They contain some portion of the glycosyl moiety of natural nucleosides and are collectively termed acyclic nucleosides and (2) the more active compounds all contain the aglycon guanine.

A recent perspective[3] reviewed the immunomodulatory properties of many 8-substituted guanosine derivatives and analogs. One of the more studied guanosine analogs with demonstrated immunomodulatory activity is 5-amino-3-($\beta$-D-ribofuranosylthiazolo[4,5-d]pyrimidine-2,7 (3H, 6H)-dione (7-thia-8-oxoguanosine)[3-7]. This nucleoside shows a broad spectrum of antiviral activity in the host animal but is virtually inactive in vitro[3]. Additionally, certain alkyl guanine analogs and derivatives were found to have similar activity profiles[8-9]. This latter work showed that neither the ribose moiety nor a portion thereof was required for immunomodulatory activity. Active guanine analogs were prepared by appending acyclic hydrocarbons of 4-6 carbon atoms in length[8] to the heterocycle.

Two patents[4,5] have issued which cover certain glycosyl derivatives of the thiazolo[4,5-d]pyrimidine moiety. Additionally, two journal publications[6,7] describe the synthesis of glycosides of this heterocycle. Further publications[10,11] have described the synthesis of aryl derivatives of thiazolo[4,5-d]pyrimidines as antimicrobials. The original syntheses of the parent heterocycles were disclosed in 1969[12] and 1970[13].

A number of ribonucleosides bearing a 2'-fluoro substituent in the "up" (arabino) configuration has provided a host of potent agents against several DNA viruses[14-17]. The best known examples are 1-(2-deoxy-2-fiuoro-$\beta$-D-arabinofuranosyl)thymine (FMAU) and 1-(2-deoxy-2-fiuoro-$\beta$-D-arabinofuranosyl)-5-iodouracil (FIAU).

The concept of primary alkyl derivatives of guanine and guanine-like heterocycles as immunomodulators has been disclosed[8,9]. There are also a fair number of recent publications[18,29] dealing with synthesis and biological evaluation of similar heterocyclic molecules substituted with alkenes, alkynes and allenes. However, with only one exception[29] these substitutions terminate with either a phosphonate or moieties which can be phosphorylated (kinased) and thus, are designed to operate by alternate mechanisms of action when compared to the compounds of the present invention.

The present invention describes a new set of novel derivatives of thiazolo [4,5-d]pyrimidine and related heterocycles. These analogues uniquely demonstrate in vitro activity against viral infections.

REFERENCES

1. Herdewijn, P. A. M. M. *Antiviral Res.* 1992, 19, 1–14. 2. Chu, C. K.; Cutler, S. J. *J. Heterocycl. Chem.* 1986, 23, 289–319. 3. Bonnet, P. A., Robins, R. K. *J. Med. Chem.* 1993, 36, 635–653. 4. Robins, R. K., Cottam, H. B. U.S. Pat. No. 4,880,784, 1989. 5. Goodman, M. G. U.S. Pat. No. 4,746,651, 1988. 6. Nagahara, K.; Anderson, J. D.; Kini, G. D.; Dalley, N. K.; Larson, S. B.; Smee, D. F.; Jin, A.; Sharma, B. S.; Jolley, W. B.; Robins, R. K.; Cottam, H. B. *J. Med. Chem.* 1990, 33, 407–415. 7. Kini, G. D.; Anderson, J. D.; Sanghvi, Y. S.; Lewis, A. F.; Smee, D. F.; Revankar, G. R.; Robins, R. K.; Cottam, H. B. *J. Med. Chem.* 1991, 34, 3006–310. 8. Michael, M. A.; Cottam, H. B.; Smee, D. F.; Robins, R. K.; Kini, G. D. *J. Med. Chem.* 1993, 36, 3431–3436. 9. Bhattacharya, B. K.; Rao, T. S.; Lewis, A. F.; Revankar, G. R. *J. Heterocycl. Chem.* 1993, in press. 10. Badawey, E. S. A.M.; Rida, S. M.; Hazza, A. A.; Fahmy, H. T. Y.; Gohar, Y. M. *Eur. J. Med. Chem.* 1993, 28, 91–96. 11. Badawey, E. S. A.M.; Rida, S. M.; Hazza, A. A.; Fahmy, H. T. Y; Gohar, Y. M. *Eur. J. Med. Chem.* 1993, 28, 97–101. 12. Baker, J. A.; Chatfield, P. V. *J. Chem. Soc.* 1969, 603–606. 13. Baker, J. A.; Chatfield, P. V. *J. Chem. Soc.* 1970, 2478–2484. 14. Watanabe, K. A.; Reichman, U.; Hirota, K.; Lopez, C; Fox, J. J. *J. Med. Chem.* 1979, 22, 21–24. 15. Fox, J. J.; Lopez, C.; Watanabe, K. A. in "Medicinal Chemistry Advances", De Las Heras, F. G.; Beg., S. eds., Pergamon Press, New York, 1981, 27–40. 16. Lopez, C.; Watanabe, K. A.; Fox, J. J. *Antimicrob. Agents Chemother.* 1980, 17, 803–806. 17. Colacino, J. M.; Lopez, C. *Antimicrob. Agents Chemother.* 1985, 28, 252–258. 18. Verheggen, I; Van Aerschot, A.; Toppet, S.; Snoeck, R.; Janssen, G.; Balzarini, J.; De Clercq, E.; Herdewijn, P. *J. Med. Chem.* 1993, 36, 2033–2040. 19. Hayashi, S.; Phadtare, S.; Zemlicka, J.; Matsukura, M.; Mitsuya, H.; Broder, S. *Proc. Natl. Acad. Sci. USA* 1988, 85, 6127–6131. 20. Larsson, A.; Stenberg, K.; Ericson, A-C.; Haglund, U.; Yisak, W-A.; Johansson, N. G.; Oberg, B.; Datema, R. *Antimicrob. Agents Chemother.* 1986, 30, 598–605. 21. Phadtare, S.; Zemlicka, J. *J. Am. Chem. Soc.* 1989, 111, 5925–5931. 22. Ashton, W. T.; Meurer, L. C.; Cantone, C. L.; Field, A. K.; Hannah, J; Karkas, J. D.; Lion, R.; Patel, G. F.; Perry, H. C.; Wagner, A. F.; Walton, E.; Tolman, R. L. *J. Med. Chem.* 1988, 31, 2304–2315. 23. Halazy, S.; Danzin, C.; Nave, J-F. European Patent Application No. 91402427.8. 24. Phadtare, S.; Zemlicka, J. *J. Med. Chem.* 1987, 30, 437–440. 25. Phadtare, S.; Kessel, D.; Corbet, T. H.; Renis, H. E.; Court, B. A.; Zemlicka, J. *J. Med. Chem.* 1991, 34, 421–127 429. 26. Megati, S.; Phadtare, S.; Zemlicka, J. *J. Org. Chem.* 1992, 57, 2320–2327. 27. Haines, D. R.; Tseng, C. K. H.; Marquez, V. E. *J. Med. Chem.* 1987, 30, 943–947. 28. Harnden, M. R.; Parkin A.; Parratt, J.; Perkins, R. M. *J. Med. Chem.* 1993, 36, 1343–1355. 29. Borcherding, D. R., Narayanan, S.; Hasobe, M.; McKee, J. G.; Keller, B. T.; Borchardt, R. T. *J. Med. Chem.* 1998, 31, 1729–1738. 30. Robins, M. J.; Hatfield, P. W. *Can. J. Chem.* 1982, 60, 547. 31. Katritzky, A. R.; Nowak-Wydra, B.; Marson, C. M. *Chem. Scrip.* 1987, 27, 477. 32. Tann, C. H.; Brodfueher, P. R.; Brundidge, S. P.; Sapino, Jr., C.; Howell, H. G. *J. Org. Chem.* 1985, 50, 33644–3647. 33. Shipman, C., Jr.; Smith, S. H.; Carlson, R. H.; Drach, J. C. *Antimicro. Agents Chemother.* 1976, 9, 120. 34. Turk, S. R.; Shipman, C., Jr.; Nassiri, M. R.; Genzlinger, G.; Krawczyk, S. H.; Townsend, L. B.; Drach, J. C. *Antimicro. Agents Chemother.* 1987, 31, 544.

SUMMARY OF THE INVENTION

The object of the present invention is provision of antiviral compounds.

A further object of the present invention is a method for treating antiviral disease.

Thus, in accomplishing the foregoing objects, there are provided in accordance with one aspect of the present invention, a compound for treating a pathophysiological state caused by a virus comprising an antiviral guanine analog having the structure

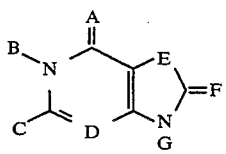

wherein
A is O, S or Se
B is H, CH₃ or NH₂
C is NH₂ or SCH₃
D is N or CH
E is O, S or Se
F is O, S or Se

| G is | —CH=CHBr | —C(CH₃)=CHCH₃ |
|---|---|---|
| | —CH₂CH=CH—CH₂CH₃ (cis & trans) | —CH₂C≡C—CH₂CH₃ |
| | —CH₂—CH=CH(CH₃)₂ | —CH₂—O—(CH₂)₂OH |
| | —(CH₂)₂CH=CH(CH₃)₂ | —CH₂—O—CH(CH₂OH)₂ |
| | —(CH₂)₃CH=CH₂ | —CH₂—O—CH₂CH=CH₂ |
| | —CH₂CH=CH—CH=CHCH₃ | —CH(CH₂CH₃)₂ |
| | —CH₂CH=C=CHCH₃ | —CH[(CH₂)₃CH₃]₂ |
| | —CH=C=CH—CH₂CH₃ | —CH[(CH₂)₄CH₃]₂ |
| | —(CH₂)₄OH | —(CH₂)₆NH₂ |
| | —CH₂—CHOH—CH₂OH | —(CH₂)₆Cl |
| | —CH₂—CH(CH₂OH)—O—CH₂PO₃H₂ | —(CH₂)₄CN |
| | —CH₂—CH=CH(CH₂)₂OH (cis & trans) | —(CH₂)₄COOH |
| | —CH₂—CH=CH(CH₂)₂PO₃H₂ (cis & trans) | —(CH₂)₄CONH₂ |

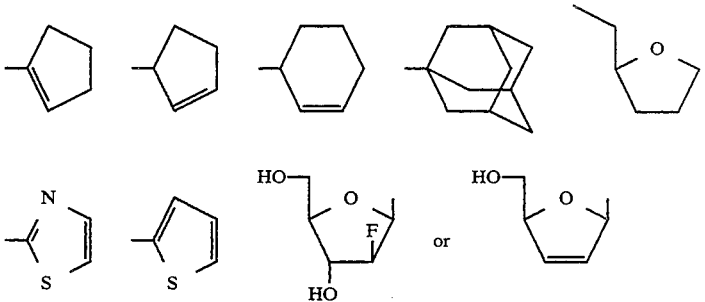

and pharmaceutically acceptable salts thereof.

Additional embodiments include a compound for treating a pathophysiological state caused by a virus comprising an antiviral guanine analog having the structure

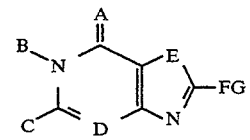

wherein,
A is O, S or Se
B is H, CH₃ or NH₂
C is NH₂ or SCH₃
D is N or CH
E is O, S or Se
F is O, S, Se or NH

| G is | —CH=CHBr | —C(CH₃)=CHCH₃ |
|---|---|---|
| | —CH₂CH=CH—CH₂CH₃ (cis & trans) | —CH₂C≡C—CH₂CH₃ |
| | —CH₂—CH=CH(CH₃)₂ | —CH₂—O—(CH₂)₂OH |
| | —(CH₂)₂CH=CH(CH₃)₂ | —CH₂—O—CH(CH₂OH)₂ |
| | —(CH₂)₃CH=CH₂ | —CH₂—O—CH₂CH=CH₂ |
| | —CH₂CH=CH—CH=CHCH₃ | —CH(CH₂CH₃)₂ |
| | —CH₂CH=C=CHCH₃ | —CH[(CH₂)₃CH₃]₂ |
| | —CH=C=CH—CH₂CH₃ | —CH[(CH₂)₄CH₃]₂ |
| | —(CH₂)₄OH | —(CH₂)₆NH₂ |
| | —CH₂—CHOH—CH₂OH | —(CH₂)₆Cl |
| | —CH₂—CH(CH₂OH)—O—CH₂PO₃H₂ | —(CH₂)₄CN |
| | —CH₂—CH=CH(CH₂)₂OH (cis & trans) | —(CH₂)₄COOH |
| | —CH₂—CH=CH(CH₂)₂PO₃H₂ (cis & trans) | —(CH₂)₄CONH₂ |

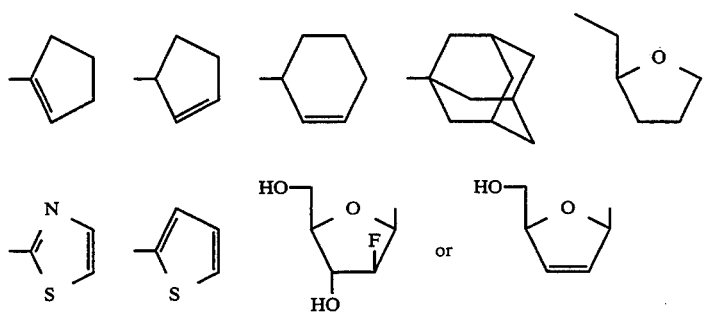

and pharmaceutically accepted salts thereof.

A further embodiment includes a compound for treating a pathophysiological state caused by a virus comprising an antiviral guanine analog having the structure

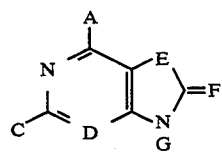

wherein
A is $NH_2$, OH, NHOH, $OCH_3$ or $SCH_3$
C is H, Br, Cl, $NH_2$ or $SCH_3$
D is N or CH
E is O, S or Se
F is O, S or Se In specific embodiments the above compounds are combined with a physiological carrier for the treatment of the pathophysiological state.

Further embodiments include methods of using the compounds to treat a viral disease.

An additional embodiment encompasses combination therapy wherein one of the above compounds is combined with a second therapeutic compound usually from the group consisting of acyclovir, HBG and ganciclovir.

Other and further objects, features and advantages will be apparent from the following description of the presently preferred embodiments of the invention given for the purpose of disclosure when taken in conjunction with the accompanying drawings.

| G is | |
|---|---|
| —CH=CHBr | —C(CH$_3$)=CHCH$_3$ |
| —CH$_2$CH=CH—CH$_2$CH$_3$ (cis & trans) | —CH$_2$C≡C—CH$_2$CH$_3$ |
| —CH$_2$—CH=CH(CH$_3$)$_2$ | —CH$_2$—O—(CH$_2$)$_2$OH |
| —(CH$_2$)$_2$CH=CH(CH$_3$)$_2$ | —CH$_2$—O—CH(CH$_2$OH)$_2$ |
| —(CH$_2$)$_3$CH=CH$_2$ | —CH$_2$—O—CH$_2$CH=CH$_2$ |
| —CH$_2$CH=CH—CH=CHCH$_3$ | —CH(CH$_2$CH$_3$)$_2$ |
| —CH$_2$CH=C=CHCH$_3$ | —CH[(CH$_2$)$_3$CH$_3$]$_2$ |
| —CH=C=CH—CH$_2$CH$_3$ | —CH[(CH$_2$)$_4$CH$_3$]$_2$ |
| —(CH$_2$)$_4$OH | —(CH$_2$)$_6$NH$_2$ |
| —CH$_2$—CHOH—CH$_2$OH | —(CH$_2$)$_6$Cl |
| —CH$_2$—CH(CH$_2$OH)—O—CH$_2$PO$_3$H$_2$ | —(CH$_2$)$_4$CN |
| —CH$_2$—CH=CH(CH$_2$)$_2$OH (cis & trans) | —(CH$_2$)$_4$COOH |
| —CH$_2$—CH=CH(CH$_2$)$_2$PO$_3$H$_2$ (cis & trans) | —(CH$_2$)$_4$CONH$_2$ |

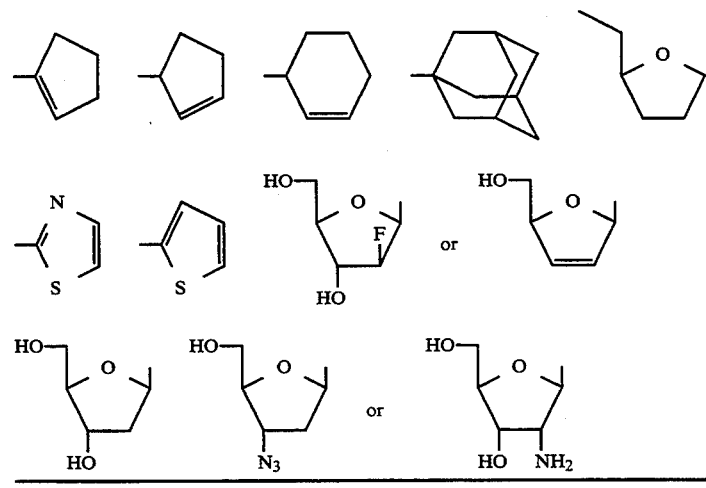

and pharmaceutically acceptable salts thereof.

Figure 2:
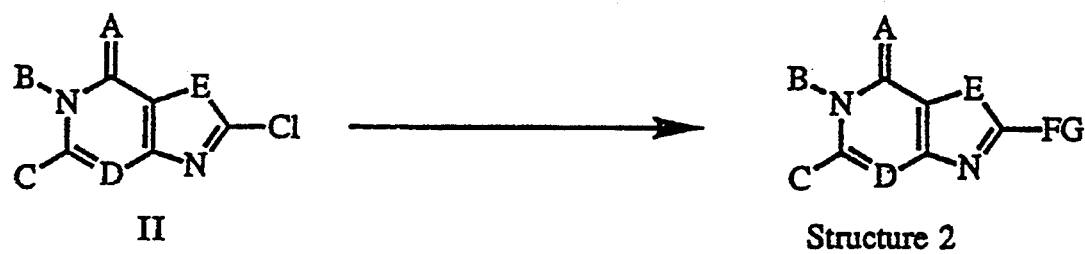

FIG. 2 is a schematic of the synthesis of structure 2.

Figure 3:
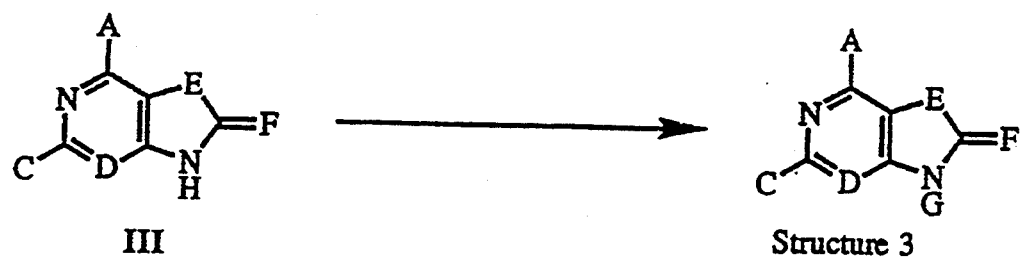

FIG. 3 is a schematic of the synthesis of structure 3.

Figure 4:
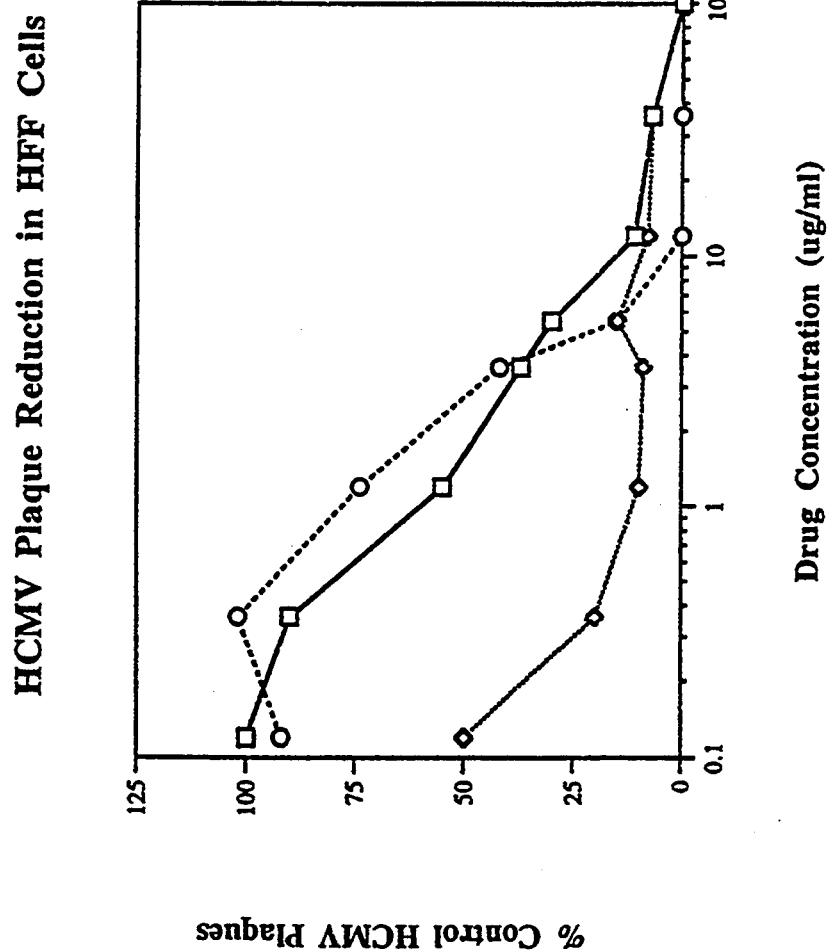

FIG. 4 is a dose response curve showing the ability of guanine analogs to inhibit HCMV production in acute infection assays.

Figure 5:
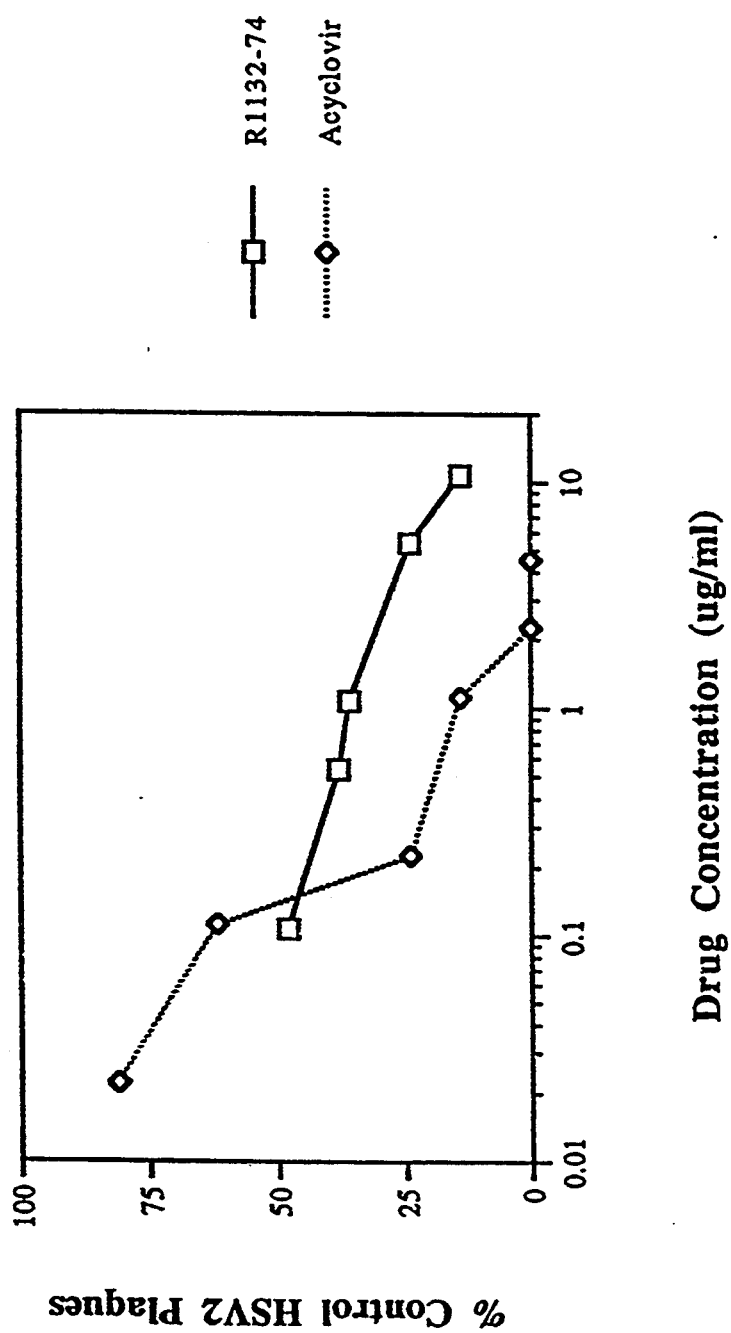

FIG. 5 is a dose response curve showing guanine analog inhibition of HSV in culture.

The drawings are not necessarily to scale. Certain features of the invention may be exaggerated in scale or shown in schematic form in the interest of clarity and conciseness.

DETAILED DESCRIPTION

It is readily apparent to one skilled in the art that various substitutions and modifications may be made to the invention disclosed herein without departing from the scope and spirit of the invention.

As used herein a physiological carrier means any of the carriers commonly used in the pharmaceutical industry for mixing of drugs used in the treatment of human and non-human animals. Examples of physiological carriers are well known to those skilled in the art. Examples of physiological carriers which will be useful in the present invention include: sodium bicarbonate, saline, buffered saline, glycerol, demethyl sulforide, liposomes and other lipid carriers.

As used herein the term "effective dose" refers to the dose of a compound when introduced into an animal to be treated (either human or non-human) produces a sufficient effect on the virus present in the pathophysiological state to interfere with the proliferation of the virus. The dose will depend upon the drug as well the virus being treated. One skilled in the art can readily determine the dose once the specific treatment parameters are determined. An effective dose is a sufficient amount of the drug such that there will be a biological inhibition of the viral infection. The effective dose of the present invention can be determined by assessing the effects of the test compound on viral infection in tissue culture (see Example 33) and in animal models (for example the SCID/hu mouse model for HIV, mouse encephatitis model for HSV and the mouse CMV model for CMV) or any other method known to those of ordinary skill in the art.

Administration of the compounds useful in the method of the present invention may be by topical, parental, oral, internasal, intravenous, intramuscular, subcutaneous or any other suitable means. The dosage administered depends upon the age and weight of patients, and kind of concurrent treatment, if any, and nature of the viral condition. Effective compounds useful in the method of the present invention may be employed in such forms as capsules, tablets, liquids, solids, suspensions or elixirs for all administrations or sterile liquid form such as solution, suspensions or emulsions, An inert carrier is preferable. Examples of inert physiological carriers include saline, phosphate buffer saline or any such carrier in which a compound used in the method of the present invention has suitable solubility properties. The physiologically effective carriers of the present invention include any solvent with which the compounds of the present invention are compatible and which are non-toxic to the individuals treated at the amounts administered.

The compounds of the present invention can also be administered as encapsulated composition.

Figure 1:
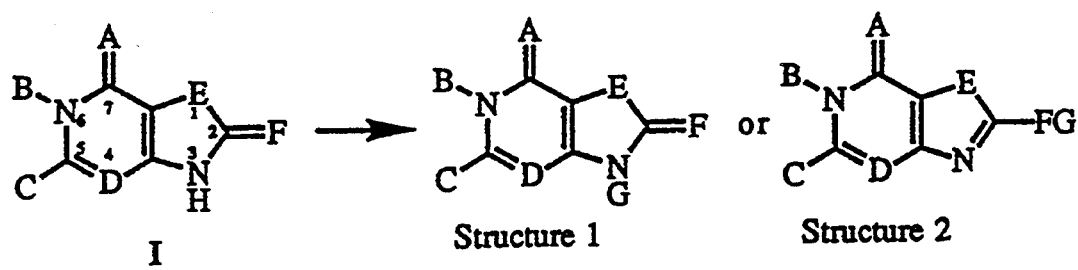
FIG. 1 is a schematic of the synthesis of structures 1 and 2.

The basic structure specific molecules we are seeking to protect are shown by structures 1-3 in FIGS. 1-3.

In general their synthesis are described below:

FIG. 1 shows the appropriate heterocycle (I), unsubstituted at the 3 position. This material is converted to its sodium salt and then allowed to react with the appropriate G-halide. The reaction temperature can vary with the reactivity of the halide used. When F=O, only compounds of Structure 1 are obtained (see Examples 1, 3, 5-8, 10-14, 16, 17 below); whereas, when F=S or Se either Structures 1 (see Examples 24 and 25 below) or Structure 2 (see Example 23 below) can be obtained by selecting the appropriate reaction temperature. For some molecules the removal of functional protecting groups may be necessary following the attachment of the appropriate G moiety to the heterocycle (see Examples 2, 4 and 9 below) and in yet other cases the desired G may be obtained by chemical manipulation after attachment of a precursor molecule to the heterocycle (see Example 15 below).

FIG. 1 shows the appropriate heterocycle (I), unsubstituted at the 3 position. This compound is converted into its trimethylsilyl derivative and then allowed to react with an appropriately protected pentofuranosyl bromide (or acetate) in either acetonitrile or chloroform (see Examples 20 and 26 below). The reaction time and temperature can vary with the reactivity of the carbohydrate employed. After isolation of the protected nucleoside by column chromatography, deprotection is accomplished by the treatment with either methanolic ammonia or sodium methoxide in methanol to obtain the free pentofuranoside (see Examples 21 and 26 below).

In FIG. 1 the B moiety of either Structure 1 or Structure 2 may be changed by chemical manipulation after attachment of the desired G (or precursor) moiety (see Example 18 below).

In FIG. 2 the Structure 2 compounds illustrate where F=NH, the appropriate G-amine or a precursor molecule is allowed to react with a 2-chloro derivative (II) of the desired heterocycle (see Example 19 below).

In FIG. 3 the appropriate heterocycle (III), unsubstituted at the 3 position, is converted to its sodium salt and then allowed to react with the appropriate G-halide. The reaction temperature can vary with the reactivity of the halide used. For some molecules the removal of functional protecting groups may be necessary following the attachment of the appropriate G moiety to the heterocycle and in yet other cases the desired G may be obtained by chemical manipulation after attachment of a precursor molecule to the heterocycle. Further, the desired A, C or F moiety may be obtained by chemical manipulation of the heterocyclic moiety after attachment of the G moiety.

One specific embodiment of the present invention is a compound for treating the pathophysiological state caused by a virus comprising an antiviral guanine analog having the structure

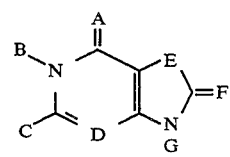

wherein,
A is O, S or Se
B is H, $CH_3$ or $NH_2$
C is $NH_2$ or $SCH_3$

D is N or CH
E is O, S or Se
F is O, S or Se

| G is | —CH=CHBr | —C(CH₃)=CHCH₃ |
|---|---|---|
| | —CH₂CH=CH—CH₂CH₃ (cis & trans) | —CH₂C≡C—CH₂CH₃ |
| | —CH₂—CH=CH(CH₃)₂ | —CH₂—O—(CH₂)₂OH |
| | —(CH₂)₂CH=CH(CH₃)₂ | —CH₂—O—CH(CH₂OH)₂ |
| | —(CH₂)₃CH=CH₂ | —CH₂—O—CH₂CH=CH₂ |
| | —CH₂CH=CH—CH=CHCH₃ | —CH(CH₂CH₃)₂ |
| | —CH₂CH=C=CHCH₃ | —CH[(CH₂)₃CH₃]₂ |
| | —CH=C=CH—CH₂CH₃ | —CH[(CH₂)₄CH₃]₂ |
| | —(CH₂)₄OH | —(CH₂)₆NH₂ |
| | —CH₂—CHOH—CH₂OH | —(CH₂)₆Cl |
| | —CH₂—CH(CH₂OH)—O—CH₂PO₃H₂ | —(CH₂)₄CN |
| | —CH₂—CH=CH(CH₂)₂OH (cis & trans) | —(CH₂)₄COOH |
| | —CH₂—CH=CH(CH₂)₂PO₃H₂ (cis & trans) | —(CH₂)₄CONH₂ |

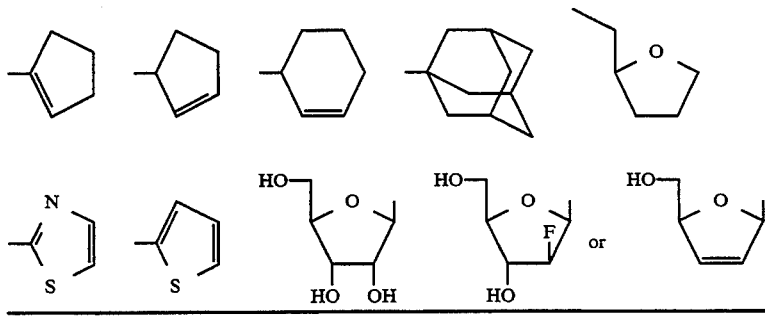

and pharmaceutically acceptable salts thereof.

Alternative embodiment includes a compound of the structure

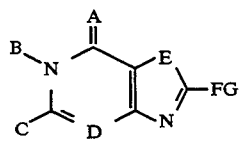

wherein,
A is O, S or Se
B is H, CH₃ or NFI₂
C is NH₂ or SCH₃
D is N or CH
E is O, S or Se
F is O, S, Se or NH

| G is | —CH=CHBr | —C(CH₃)=CHCH₃ |
|---|---|---|
| | —CH₂CH=CH—CH₂CH₃ (cis & trans) | —CH₂C≡C—CH₂CH₃ |
| | —CH₂—CH=CH(CH₃)₂ | —CH₂—O—(CH₂)₂OH |
| | —(CH₂)₂CH=CH(CH₃)₂ | —CH₂—O—CH(CH₂OH)₂ |
| | —(CH₂)₃CH=CH₂ | —CH₂—O—CH₂CH=CH₂ |
| | —CH₂CH=CH—CH=CHCH₃ | —CH(CH₂CH₃)₂ |
| | —CH₂CH=C=CHCH₃ | —CH[(CH₂)₃CH₃]₂ |
| | —CH=C=CH—CH₂CH₃ | —CH[(CH₂)₄CH₃]₂ |
| | —(CH₂)₄OH | —(CH₂)₆NH₂ |
| | —CH₂—CHOH—CH₂OH | —(CH₂)₆Cl |
| | —CH₂—CH(CH₂OH)—O—CH₂PO₃H₂ | —(CH₂)₄CN |
| | —CH₂—CH=CH(CH₂)₂OH (cis & trans) | —(CH₂)₄COOH |
| | —CH₂—CH=CH(CH₂)₂PO₃H₂ (cis & trans) | —(CH₂)₄CONH₂ |

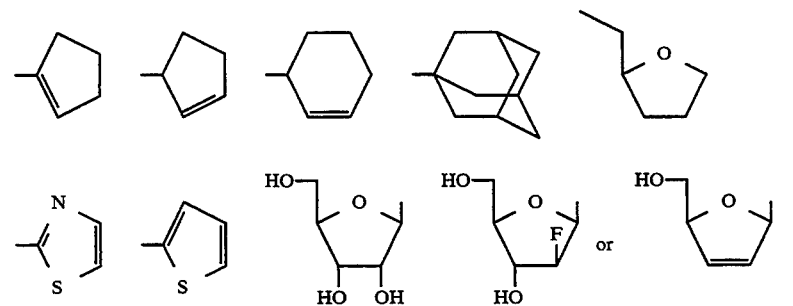

and pharmaceutically acceptable salts thereof.

Another alternative compound for treating the pathophysiological state caused by a virus comprised is the structure

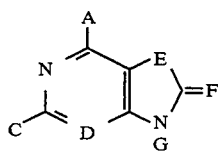

wherein,

A is NH₂, OH, NHOH, OCH₃ or SCH₃
C is H, Br, Cl, NH₂ or SCH₃
D is N or CH
E is O, S or Se
F is O, S or Se an effective amount of at least one of the compounds above admixed with the physiological carrier, Another embodiment to the present invention is a combination therapy, In this method an effective amount of at least one of the compounds of the present invention is combined with an effective amount of a second therapeutic compound and this combination is admixed with a physiological carrier, These combinations can be used for enhanced treatment of a variety of viral infections. The second therapeutic compound is usually selected from the group consisting of acyclovir, HBG and ganciclovir.

Another embodiment of the present invention is a method for treating pathophysiological state caused by

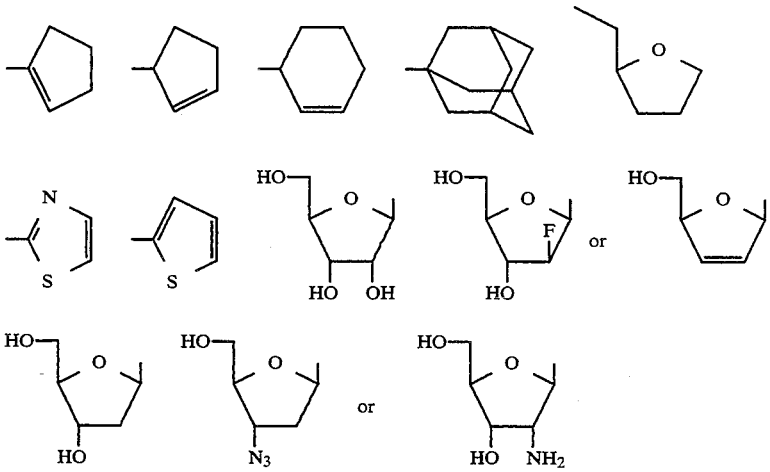

and pharmaceutically acceptable salts thereof. In a specific embodiment of the present invention a compound of the structure

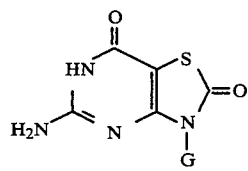

wherein,

G is —CH₂CH=CH—CH₂CH₃ (trans) —CH₂—CH=CH(CH₃)₂ —(CH₂)₃CH=CH₂ —CH[(CH₂)₃CH₃]₂ —CH[(CH₂)₄CH₃]₂ or —CH(CH₂CH₃)₂ and pharmaceutically acceptable salts thereof are used for the treatment of cytomegalovirus.

An alternative embodiment of the present invention is a composition for treating viral infection comprised of a virus comprising the step of administering the composition or the combination to a human or non-human animal.

The compounds compositions, combinations or pharmaceutical salts thereof of the present invention can be used for treatment of a variety of viral diseases. Examples of specific viral diseases which can be treated includes those caused by herpes simplex virus type 1, herpes simplex virus type 2, human herpes virus type 6, human herpes virus type 7, human cytomegalovirus, Epstein-Bar virus, HIV-1, HIV-2 and varicella-zoster virus.

The compounds compositions, combinations or pharmaceutical salts thereof of the present invention are also useful in the treatment of the hepatotropic viruses consisting of hepatitis A, hepatitis B, hepatitis C, hepatitis E and delta virus.

The following examples are offered by way of illustration are not intended to limit invention in any manner.

EXAMPLE 1

5-Amino-3-(2-acetoxyethoxymethyl)thiazolo-[4,5-d]pyrimidine-2,7(3H,6H)-dione

5-Aminothiazolo[4,5-d]pyrimidine-2,7(3H,6H)-dione[13] (1, 0.53 g, 2.88 mmol) was mixed with anhydrous DMF (20 mL). The mixture was protected from moisture and NaH (80% dispersion in mineral oil, 87 mg, 2.9 mmol) was added. The mixture was stirred at ambient temperature for 2 h and then cooled in an ice bath. (2-Acetoxyethoxy)methyl bromides[30] (0.35 mL, 3.02 mmol) was added over a 5 min period and the mixture was stirred in the cold for 30 rain more. The solution was evaporated in vacuum and then 25 mL of $H_2O$ was added. The pH of the mixture was adjusted to 6 by the addition of AcOH and then the mixture was stored in the cold (5° C.) for 16 h. The solid produced was collected by filtration and then was extracted with hot MeOH (50 mL). Silica gel (10 g) was added to the MeOH solution which was then evaporated. The dry powder was placed on top of a silica gel column (5.5×12 cm) and the column was eluted with progressively increasing concentrations of MeOH in $CH_2Cl_2$ (%MeOH, vol in L): (0,0.5); (1,0.5); (2,0.5); (5,2). Eluate containing the product was evaporated and the residue was crystallized from an EtOH:$H_2O$ mixture, then dried in vacuum at 80° C. for 2 d; 80 mg (266 μmol, 28%), mp 173°–176 ° C. Ir (KBr): $\nu$3520, 3450, 3350 and 3250 (NH, $NH_2$), 1720 (C=O, ester), 1675 (C=O), and 1640 (C=C, C=N) $cm^{-1}$. Uv, $\lambda_{max}$ (nm), ($\ominus \times 10^{-3}$): pH 1,300 (8.95), 248 (8.39), 216 (25.8); MeOH, 302 (8.49), 246 (8.10), 216 (24.0); pH 11, 290 (6.88), 246 (7.52). $^1H$ nmr (DMSO-$d_6$): δ 1.98 (s, 3 H, $CH_3$), 3.74 (t, 2 H, $CH_2OCH_2$), 4.09 (t, 2 H, C(O)$OCH_2$), 5.16 (s, 2 H, $NCH_2O$), 6.97 (br s 2 H, $NH_2$), and 11.18 (br s, 1 H, NH). Anal. Calc'd for $C_{10}H_{12}N_4O_5S$ (300.29): C, 40.00; H, 4.03; N, 18.66. Found: C, 39.79; H, 4.07; N, 18.36.

EXAMPLE 2

5-Amino-3-(2-hydroxyethoxymethyl)thiazolo[4,5-d]-pyrimidine-2,7(3H,6H)-dione

A mixture of 5-Amino-3-(2-hydroxyethoxymethyl)thiazolo[4,5-d]pyrimidine-2,7(3H,6H)-dione (300 mg, 999 μmol) and conc. $NH_4OH$ (10 mL) was placed in a pressure bottle and stirred at ambient temp for 3 h. The solution was evaporated under vacuum and the residual solid was stirred with $H_2O$ (10 mL). The mixture was neutralized (HOAc) and the solid was collected by filtration and then dried in vacuum over $P_2O_5$ for 20 h; 145 mg (560 μmol, 56%). The solid was crystallized from $H_2O$ and then dried in a vacuum at 70° C. for 2d; mp 230°–232° C. IR (KBr): $\nu$ 3305 and 3180 (OH, NH, $NH_2$), and 1650 broad (C=O, C=N) $cm^{-1}$. Uv, $\lambda_{max}$ (nm), ($\epsilon \times 10^{-3}$): pH 1,300 (9.93), 248 (9.26), 216 (28.5); $H_2O$, 300 (9.74), 248 (9.08), 216 (28.1); pH 11, 290 (7.70), 246 (8.38), 226 (7.37). $^1H$ nmr (DMSO-$d_6$): δ 3.45 (t, 2 H, $CH_2$), 3.54 (t, 2 H, $CH_2$), 4.63 (t, 1 H, OH), 5.14 (s, 2 H, $OCH_2N$), 6.95 (br s, 2 H, $NH_2$) and 11.2 (br s, 1 H, NH). Anal. Calc'd for $C_8H_{10}N_4O_4S$ (258.26): C, 37.21; H, 3.90; N, 21.69. Found: C, 37.15; H, 3.88; N, 21.29.

EXAMPLE 3

5-Amino-3-(4-acetoxybutyl)thiazolo[4,5-d]-pyrimidine-2, 7 (3H,6H)-dione

5-Aminothiazolo[4,5-d]pyrimidine-2,7(3H,6H)-dione[13] (1, 0.46 g, 2.5 mmol) was mixed with anhydrous DMF (25 mL). The mixture was protected from moisture and NaH (80% dispersion in mineral oil, 76 mg, 2.53 mmol) was added. The mixture was stirred at ambient temperature for 1 h. 4-Bromobutyl acetate (0.4 mL, 2.76 mmol) was added and the mixture was heated at 75°–80° C. (oil bath) for 4h. The mixture was evaporated in vacuum and the residue was stirred with $H_2O$ (25 mL) to produce a solid. The solid was collected by filtration, crystallized from a MeOH-$H_2O$ mixture and then dried in vacuum over $P_2O_5$ for 2d; 0.38 g (1.27 mmol, 51%), mp 189°–190° C. Ir (KBr): $\nu$ 3420, 3320 and 3220 (NH, $NH_2$), 1730 (C=O), and 1705 (C=O) $cm^{-1}$. Uv, $\lambda_{max}$ (nm), ($\epsilon \times 10^{-3}$): pH 1, 302 (9.35), 250 (8.18), 222 (29.9); MeOH, 302 (9.31), 248 (8.71), 222 (29.3); pH 11, 292 (7.93), 250 (7.67), 224 (11.3). $^1H$ nmr (DMSO-$d_6$): δ 1.54-1.58 (m, 2 H, $CH_2$), 1.65-1.70 (m, 2 H, $CH_2$), 1.98 (s, 3 H, $CH_3$), 3.78 (t, 2 H, $NCH_2$), 4.01 (t, 2 H, $OCH_2$), 6.81 (br s, 2 H $NH_2$), and 10.97 (br s, 1 H, NH). Anal. Calc'd for $C_{11}H_{14}N_4O_4S$ (298.32): C, 44.29; H, 4.73; N, 18.78. Found: C, 44.09; H, 4.76; N, 18.57.

EXAMPLE 4

5-Amino-3-(4-hydroxybutyl)thiazolo[4,5-d]-pyrimidine-2,7(3H, 6H)-dione

A mixture of 5-Amino-3-(4-acetoxybutyl)-thiazolo[4,5-d]pyrimidine-2,7(3H,6H)-dione (230 mg, 771 izmol) and conc. $NH_4OH$ (10 mL) was placed in a pressure bottle and stirred at ambient temperature for 18 h. The solution was evaporated under vacuum and the residual solid was stirred with $H_2O$ (10 mL). The solid was collected by filtration, crystallized from a MeOH:$H_2O$ mixture and dried in vacuum at 80° C. for 3 d; 120 mg (468 μmol, 61%), mp 258°–260° C. Ir (KBr): $\nu$ 3305 and 3189 (OH, NH, $NH_2$), and 1650 broad (C=O, C=N) $cm^{-1}$. Uv, $\lambda_{max}$ (nm), ($\epsilon \times 10^{-3}$): pH 1, 302 (9.83), 250 (8.47), 222 (30.3); $H_2O$, 302 (9.70), 250 (8.37), 222 (30.4); pH 11, 292 (7.71), 250 (7.47), 224 (9.62). $^1H$ nmr (DMSO-$d_6$): δ1.35-1.42 (m, 2 H, $CH_2$), 1.60-1.68 (m, 2 H, $CH_2$), 3.38 (m, 2 H, $OCH_2$), 3.76 (t, 2 H, $NCH_2$), 4.40 (t, 1 H, OH), 6.89 (br s, 2 H, $NH_2$), and 11.06 (br s, 1 H, NH). Anal. Calc'd for $C_9H_{12}N_4O_3S$ (256.28): C, 42.18; H, 4.72; N, 21.86. Found: 42.05; H, 4.67; N, 21.72.

EXAMPLE 5

5-Amino-3-(pent-4-ene-1-yl)thiazolo[4,5-d]-pyrimidine-2,7(3H, 6H)-dione

5-Aminothiazolo[4,5-d]pyrimidine-2,7(3H,6H)-dione[13] (390 mg, 2.12 mmol) was mixed with anhydrous DMF (20 mL) and NaH (80% dispersion in mineral oil, 64 mg, 2.13 mmol). The mixture was protected from moisture and stirred at ambient temperature for 0.5 h. 5-Bromo-1-pentene (0.26 mL, 2.2 mmol) was added and the mixture was heated at 75°±3° C. (oil bath) for 2 h. After cooling, the mixture was evaporated in vacuum and then $H_2O$ (50 mL) was added. The solid produced was collected by filtration, crystallized from a MeOH:$H_2O$ mixture and dried in vacuum at 80° C. for 16 h; 300 mg (1.19 mmol, 56%), mp 240°–243 ° C. Ir (KBr): $\nu$ 3480, 3380 and 3360 (NH, $NH_2$), and 1730 (C=O) $cm^{-1}$. Uv, $\lambda_{max}$ (nm), ($\epsilon \times 10^{-3}$): pH 1, 302 (9.50), 250 (8.13), 222 (28.4); MeOH, 302 (9.01), 248 (8.41), 222 (28.1); pH 11, 292 (7.76 250 (7.49), 226 (11.6). $^1H$ nmr (DMSO-$d_6$): δ 1.68-1.75 (m, 2 H, $CH_2$), 2.00-2.06 (m, 2 H, $CH_2$), 3.75 (t, 2 H, $NCH_2$), 4.97 (d, i H, $CHCH_2$), 5.05 (d, 1 H, $CHCH_2$), 5.78-5.85 (m, 1 H, $CH_2CH$), 6.91 (br s, 2 H, $NH_2$), and 11.09 (br s, 1 H, NH). Anal. Calc'd for C$_{10}$H$_{12}$N$_4$O$_2$S (252.3): C, 47.61; H, 4.79; N, 22.21. Found: C, 47.88; H, 4.83; N, 22.00.

EXAMPLE 6

5-Amino-3-(pent-2-ene-1-yl)thiazolo[4,5-d]-pyrimidine-2,7(3H,6H)-dione

A mixture of 5-aminothiazolo[4,5-d]pyrimidine-2,7 (3H, 6H)-dione[13] (440 mg, 2.39 mmol), NaH (80% dispersion in mineral oil, 73 mg, 2.43 mmol) and anhydrous DMF (20 mL) was protected from moisture and stirred at ambient temperature for 0.5 h. 1-Bromo-2-pentene (0.34 mL, 2.87 mmol) was added and the mixture was heated at 75°±3° C. for 4 h. After cooling, the mixture was evaporated in vacuum and then H$_2$O (20 mL) was added. The mixture was stirred for 15 min and then solid was collected by filtration, crystallized from a MeOH:H$_2$O mixture and dried in vacuum at 80° C. for 16 h; 420 mg (1.65 mmol, 69%), mp 240°-243° C. Ir (KBr): $\nu$ 3450 and 3340 (NH, NH$_2$), and 1650 broad (C=O, C=N, C=C) cm$^{-1}$. Uv, $\lambda$ $_{max}$ (nm), ($\epsilon \times 10^{-3}$): pH 1, 302 (10.3), 250 (9.08), 222 (30.6); MeOH, 302 (9.52), 250 (9.09), 222 (29.5); pH 11, 292 (8.44), 248 (8.29), 226 (12.9). $^1$H nmr (DMSO-d$_6$): $\delta$ 0.947 (t, 3 H, CH$_3$), 2.14-2.22 (m, 2 H, CH$_3$CH$_2$), 4.38 (d, 2 H, NCH$_2$), 5.35-5.40 (m, 1 H, CHCH), 5.52-5.58 (m, 1 H, CHCH), 6.87 (br, 2 H, NH$_2$) and 11.1 (br s, 1 H, NH). Anal. Calc'd for C$_{10}$H$_{12}$N$_4$O$_2$S·0.1 H$_2$O (254.10): C, 47.27; H, 4.84; N, 22.04. Found: C, 46.94; H, 4.70; N, 22.29.

EXAMPLE 7

5-Amino-3-(3-methylbut-2-ene-1-yl)thiazolo[4,5-d]-pyrimidine-2,7(3H,6H)-dione

A mixture of 5-aminothiazolo[4,5-d]pyrimidine-2,7(3H,6H)-dione[13] (415 mg, 2.25 mmol), anhydrous DMF (20 mL) and NaH (80% dispersion in mineral oil, 68 mg, 2.27 mmol) was stirred at ambient temperature for. 0.5 h. 4-Bromo-2-methyl-2-butene (0.27 mL, 2.34 mmol) was added and the mixture was stirred at ambient temperature for 7 h more. The mixture was evaporated in vacuum and then H$_2$O (25 mL) was added. The solid produced was collected by filtration and dried in vacuum over P$_2$O$_5$ for 16 h. The solid was dissolved in a solution of MeOH in CH$_2$Cl$_2$ (5%, 120 mL) and the resulting mixture was applied to a silica gel column (5.5×12.5 cm, packed in CH$_2$Cl$_2$). The column was eluted with 2% MeOH in CH$_2$Cl$_2$ (0.5 L), and then with 5% MeOH in CH$_2$Cl$_2$ (1.5 L). Eluate containing the homogeneous product was evaporated and the residual solid was crystallized from a MeOH:H$_2$O mixture, then dried in vacuum at 78° C. for 16 h; 73.6 mg (292 $\mu$mol, 13%), mp 290°-292° C. Ir (KBr): $\nu$ 3440, 3300 and 3190 (NH, NH$_2$), and 1640 broad (C=O, C=N, C=C) cm$^{-1}$. Uv, $\lambda$ $_{max}$ (nm), ($\epsilon \times 10^{-3}$): pH 1, 302 (9.64), 250 (8.23), 222 (28.2); MeOH, 302 (9.08), 250 (8.48), 222 (28.5); pH 11, 92 (7.92), 250 (7.88), 224 (11.5). $^1$H nmr (DMSO-d$_6$): $\delta$ 1.67 (s, 3 H, CH$_3$), 1.75 (s, 3 H, CH$_3$), 4.33 (d, 2 H, CH$_2$), 5.19-5.22 (m, 1 H, CH), 6.91 (br s, 2 H, NH$_2$), and 11.12 (br s, 1 N, NH). Anal. Calc'd for C$_{10}$H$_{12}$N$_4$O$_2$S (252.30): C, 47.61; H, 4.79; N, 22.21. Found: C, 47.71; H, 4.69; N, 21.86.

EXAMPLE 8

5-Amino-3-(2,2-dimethyl-1,3-dioxolan-4-ylmethyl)-thiazolo-[4,5-d]pyrimidine-2,7(3H, 6H)-dione A mixture of 5-aminothiazolo[4,5-d]pyrimidine-2,7(3H,6H)-dione[13] (3 g, 16.29 mmol), NaH (80% dispersion in mineral oil, 0.53 g, 17.67 mmol) and anhydrous DMF (100 mL) was protected from moisture and stirred at ambient temperature for 1 h. 4-Chloromethyl-2,2-dimethyl-1,3-dioxolane (2.4 mL, 17.54 mmol) was added and the mixture was heated at 140°±5° C. (oil bath) for 42 h. After cooling, the mixture was evaporated in vacuum and then H$_2$O (100 mL) was added. The mixture was stirred, then filtered and the aqueous flitrate was taken to dryness by continual coevaporation with EtOH. The residue was stirred with MeOH (100 mL) and then silica gel (25 g) was added and the mixture evaporated. The dry powder was placed on top of a silica gel column (5.5×21 cm) and the column was flash eluted with progressively increasing concentrations of MeOH in CH$_2$Cl$_2$ (%MeOH, volume in L): (0, 0.5); (1, 1); (2, 1); (5, 3.5); (10, 1). Eluate containing the product was evaporated and the solid was dried in vacuum for 2 d; 1.79 g (6.00 mmol, 37%).

A spectroscopically and chromatographically identical sample of the title compound obtained from a pilot reaction was dried in vacuum over P$_2$O$_5$ for 16 h; mp 222°-225° C. Ir (KBr): $\nu$ 3410, 3320, 3220, and 3150 (NH, NH$_2$), and 1680 (C=O, C=C, C=N) cm$^{-1}$. Uv, $\lambda$ $_{max}$ (nm), ($\epsilon \times 10^{-3}$): pH 1, 302 (9.02), 250 (8.17), 222 (26.9); MeOH, 302 (9.06), 250 (8.66), 222 (26.2); pH 11, 292 (7.29), 260 (6.16), 224 (9.26). $^1$H nmr (DMSO-d$_6$): $\delta$ 5 1.23 (s, 3 H, CH$_3$), 1.34 (s, 3 H, CH$_3$), 3.75-3.84 (m, 2H, CH2), 3.90-4.00 (m, 2 H, CH$_2$), 4.38-4.40 (m, 1 H, CH), 6.90 (br s, 2 H, NH$_2$), and 11.00 (br s, 1 H, NH). Anal. Calc'd for C$_{11}$H$_{14}$N$_4$O$_4$S (298.32): C, 44.29; H, 4.73; N, 18.78. Found: C, 44.15; H, 4.76; N, 18.36.

EXAMPLE 9

5-Amino-3-(2,3-dihydroxypropyl)thiazolo[4,5-d]-pyrimidine-2,7(3H,6H)-dione

A mixture of 5-amino-3-(2,2-dimethyl-1,3-dioxolan-4-ylmethyl)thiazolo[4,5-d]pyrimidine-2,7(3H,6H)-dione(200 mg, 0.67 mmol) and a solution of hydrogen chloride in MeOH (10%, 20 mL) was protected from moisture and stirred at ambient temperature for 45 min. The solution was evaporated and the residue was stirred with H$_2$O (20 mL). The mixture was immediately made basic (pH=9) by the addition of conc. NH$_4$OH and then acidified (pH=6) with AcOH. The mixture was allowed to stand for 2 h and then the solid was collected by filtration, washed with H$_2$O (50 mL) and dried in vacuum at 95° C. for 16 h.; 100 mg (0.387 mmol, 57%), mp 248°-254° C. Ir (KBr): $\nu$ 3360 broad (OH, NH, NH$_2$), and 1600 broad (C=O, C=C, C=N) cm$^{-1}$. Uv, $\lambda$ $_{max}$ (nm), ($\epsilon \times 10^{-3}$): pH 1, 302 (10.4), 250 (9.59), 222 (29.3); MeOH, 302 (9.16), 250 (8.71), 222 (26.9); pH 11, 292 (7.62), 250 (7.67), 224 $^1$H nmr (DMSO-d$_6$): $\delta$3.68-3.73 (m, 2 H, CH$_2$), 3.80-3.92 (m, 3 H, CH$_2$ and OH), 4.63 (t, 1 H, CH), 4.87 (d, 1 H, OH), 6.90 (br s, 2 H, NH$_2$) and (br s, 1 H, NH). Anal. Calc'd for C$_8$H$_{10}$N$_4$O$_4$S (258.26): C, 37.21; H, 3.90; N, 21.69. Found: C, 36.81; H, 4.02; N, 21.26.

EXAMPLE 10

5-Amino-3-(pentan-3-yl)thiazolo[4,5-d]-pyrimidine-2,7(3H, 6H)-dione

A mixture of 5-aminothiazolo[4,5-d]pyrimidine-2,7(3H,6H)-dione[13] (425 mg, 2.31 mmol), NaH (80% dispersion in mineral oil, 70 mg, 2.33 mmol) and anhydrous DMF (20 mL) was protected from moisture and stirred at ambient temperature for 1 h. 3-Bromopentane (0.3 mL, 2.42 mmol) was added and the mixture was stirred and heated at 7520 ±3° C. (oil bath) for 3 h then at 100°±3° C. for 3 h. After cooling, the mixture was evaporated in vacuum, H$_2$O (50 mL) was added and the mixture was stirred for 16 h. The solid was collected by filtration and dried in vacuum over P$_2$O$_5$. The solid was extracted with boiling MeOH (50 mL). Silica gel (10 g) was added to the MeOH extract and the mixture was evaporated. The dry powder was placed on top of a silica gel column (3.5×25 cm.). The column was flash eluted with progressively increasing concentrations of MeOH in CH$_2$Cl$_2$ (%MeOH, vol in L): (0, 0.5); (2, 0.5); (4,1). Eluate containing the homogeneous product was evaporated and the solid was dried in vacuum at 70° C. for 2 d; 105 mg (429 μmol, 18%), mp >232° C. (broad). Ir (KBr): $\nu$ 3410, 3330 and 3230 (NH, NH$_2$), and 1700-1600 broad (C=O, C=C, C=N) cm$^{-1}$. Uv, $\lambda_{max}$ (nm), ($\epsilon \times 10^{-3}$): pH 1, 304 (9.53), 250 (8.05), 224 (30.3); MeOH, 304 (9.1), 250 (8.31), 222 (27.4); pH 11, 294 (7.12), 248 (7.06), 224 (11.7). $^1$H nmr (DMSO-d$_6$): δ 0.75 (t, 3 H, CH$_3$), 1.70-1.76 (m, 2 H, CH$_2$), 2.08 (br s, 2 H, CH$_2$), 4.28 (br s, 1 H, NCH), 6.84 (br s, 2 H, NH$_2$), and 11.10 (br s, 1 H, NH). Anal. Calc'd for C$_{10}$H$_{14}$N$_4$O$_2$S (254.31): C, 47.23; H, 5.55; N, 22.03. Found: C, 47.35; H, 5.59; N, 21.75.

EXAMPLE 11

5-Amino-3-(nonan-5-yl)thiazolo[4,5-d]-pyrimidine-2,7(3H, 6H)-dione

A mixture of 5-aminothiazolo[4,5-d]pyrimidine-2,7(3H,6H)-dione[13] (440 mg, 2.39 mmol), NaH (80% dispersion in mineral oil, 73 mg, 2.43 mmol) and anhydrous DMF (20 mL) was protected from moisture and stirred at ambient temperature for 40 min. A solution of 5-bromononane[31] (550 mg, 2.66 mmol) in anhydrous DMF (5 mL) was added and the mixture was stirred and heated at 70°±3° C. (oil bath) for 4 h. After cooling, the mixture was evaporated in vacuum and then H$_2$O (50 mL) was added and the mixture was stirred for 15 min. The solid was collected by filtration and stirred with MeOH (50 mL) for 15 min. The mixture was filtered and 5 g of silica gel was added to the flitrate. The mixture was evaporated and the dry powder was placed on top of a silica gel column (3.5×24 cm.). The column was flash eluted with a progressively increasing concentration of MeOH in CH$_2$Cl$_2$ (%MeOH, vol in L): (0, 0.5); (2, 0.5); (5, 1). Eluate containing the product was evaporated and the solid was dried in vacuum at 70° C. for 2 d; 120 mg (386 μmol, 16%), mp >175° C. (broad). Ir (KBr): $\nu$ 3490, 3440, 3320 and 3220 (NH, NH$_2$), and 1700-1600 broad (C=O, C=C, C=N) cm$^{-1}$. Uv, $\lambda_{max}$ (nm), ($\epsilon \times 10^{-3}$): pH 1, 304 (9.84), 250 (8.19), 224 (29.9); MeOH, 304 (9.13), 250 (8.41), 224 (28.0); pH 11, 294 (7.52), 250 (7.36), 224 (12.6). $^1$H nmr (DMSO-d$_6$): δ 0.81 (t, 6 H, 2CH$_3$), 1.04-1.30 (m, 8 H, 4CH$_2$), 1.61-1.69 (m, 2 H, CH$_2$), 2.04 (br s, 2 H, CH$_2$), 4.41 (br s, 1 H, NCH), 6.84 (br s, 2 H, NH$_2$), and 11.11 (br s, 1 H, NH). Anal. Calc'd for C$_{14}$H$_{22}$N$_4$O$_2$S (310.42): C, 54.17; H, 7.14; N, 18.05. Found: C, 54.26; H, 7.17; N, 17.73.

EXAMPLE 12

5-Amino-3-(undecan-6-yl)thiazolo[4,5-d]-pyrimidine-2,7(3H,6H)-dione

A mixture of 5-aminothiazolo[4,5-d]pyrimidine-2,7(3H,6H)-dione[13] (460 mg, 2.5 mmol), anhydrous DMF (20 mL) and NaH (80% dispersion in mineral oil, 76 mg, 2.53 mmol) was protected from moisture and stirred at ambient temperature for 0.5 h. 6-Bromoundecane[31] (600 mg, 2.55 mmol) was added and the mixture was heated at 100°±3° C. (oil bath) for 4 h. After cooling, the mixture was evaporated in vacuum and then H$_2$O (50 mL) was added. The mixture was stirred for 15 rain and then the volume was increased to 200 mL by the addition of H$_2$O. The mixture was allowed to stand for 16 h. The solid was collected by filtration, stirred with MeOH (50 mL) and again filtered. Silica gel (10 g) was added to the MeOH solution and the mixture was evaporated. The dry power was placed on top of a silica gel column (3.5×30 cm) and the column was flash eluted with progressively increasing concentrations of MeOH in CH$_2$Cl$_2$ (% MeOH, vol in L): (0, 0.5); (1, 0.5); (2, 1); (4, 1). Eluate containing the product was evaporated and the solid was dried in vacuum at 70° C. for 2 d; 220 mg (650 μmol, 26%), mp >195° C. (broad). A portion (190 mg) of the solid was crystallized from a MeOH:H$_2$O mixture and dried at 80° C. in vacuum for 16 h: 120 mg, mp 202°-204° C. Ir (KBr): $\nu$ 3390, 3320, and 3210 (NH, NH$_2$), 1655 (C=O, C=C, C=N), and 1625 (C=O, C=C, C=N) cm$^{-1}$. Uv, $\lambda_{max}$ (nm), ($\epsilon \times 10^{-3}$): pH 1, 308 (9.32), 250 (9.26), 226 (19.9); MeOH, 304 (9.47), 250 (8.49), 224 (27.0); pH 11,294 (7.64), 250 (7.47), 224 (12.5). $^1$H nmr (DMSO-d$_6$): δ 0.805 (t, 6 H, CH$_3$), 1.12-1.23 (m, 12 H, CH$_2$), 1.61-1.68 (m, 2 H, CH2), 2.10 (br s, 2 H, CH$_2$), 4.43 (br s, 1 H, CH), 6.77 (br s, 2 H, NH$_2$), 11.01 (br s, 1 H, NH). Anal. Calc'd for C$_{16}$H$_{26}$N$_4$O$_2$S (338.48): C, 56.78; H, 7.74; N, 16.55. Found: C, 56.86; H, 7.85; N, 15.62.

EXAMPLE 13

5-Amino-3-(cyanobutyl)thiazolo[4,5-d]-pyrimidine-2,7(3H,6H)-dione

A mixture of 5-aminothiazolo[4,5-d]pyrimidine-2,7(3H,6H)-dione[13] (410 mg, 2.33 mmol), NaH (80% dispersion in mineral oil, 72 mg, 2.4 mmol) and anhydrous DMF (20 mL) was protected from moisture and stirred at ambient temperature for 1 h. 5-Bromovaleronitrile (0.29 mL, 2.48 mmol) was added and the mixture was heated at 75°±3° C. (oil bath) for 5 h. After cooling, the mixture was evaporated in vacuum and the residue was stirred with H$_2$O (20 mL). The solid was collected by filtration and then stirred with MeOH (50 mL). Silica gel (10 g) was added and the mixture was evaporated. The dry power was placed on a silica gel column (3.5×20 cm) and the column was flash eluted with progressively increasing concentrations of MeOH in CH$_2$Cl$_2$ (%MeOH, vol in L): (0, 1); (1, 1); (2, 1); (3, 1); (5, 2.5). Eluate containing the homogeneous product was evaporated and the solid was dried in vacuum at 80° C. for 16 h; 420 mg (1.58 mmol, 68%), mp 240°-243° C. Ir (KBr): $\nu$ 3430, 3330 and 3220 (NH, NH$_2$), 2250 (C-N), 1710 (C=O), and 1665 (C=N) cm$^{-1}$. Uv, $\lambda_{max}$ (nm), ($\epsilon \times 10^{-3}$): pH 1, 302 (9.53), 250 (8.42), 222 (30.1); MeOH, 302 (9.04), 250 (8.64), 220 (28.8); pH 11, 292 (7.66), 250 (7.61), 224 (10.3). $^1$H nmr (DMSO-d$_6$): δ 1.51-1.56 (m, 2 H, CH$_2$), 1.68-1.73 (m, 2 H, CH$_2$), 2.55 (t, 2 H, CH$_2$CN), 3.79 (t, 2 H, NCH$_2$), 6.93 (br s, 2 H, NH$_2$), and 11.1 (br s, 1 H, NH). Anal. Calc'd for C$_{10}$H$_{11}$N$_5$O$_2$S (265.3): C, 5.27; H, 4.18; N, 26.40. Found: C, 45.67; H, 4.09; N, 25.97.

EXAMPLE 14

5-Amino-3-[4-(ethoxycarbonyl)butyl]thiazolo[4,5-d]-pyrimidine-2,7(3H, 6H)-dione

A mixture of 5-aminothiazolo[4,5-d]pyrimidine-2,7(3H,6H)-dione[13] (400 mg, 2.17 mmol), NaH (80% dispersion in mineral oil, 70 mg, 2.33 mmol) and anhydrous DMF (20 mL) was protected from moisture and stirred at ambient temperature for 0.5 h. Ethyl 5-bromovalerate (0.37 mL, 2.34 mmol) was added and the mixture was heated at 75°±3° C. (oil bath) for 5 h. After cooling, the mixture was evaporated in vacuum and then H$_2$O (20 mL) was added. After standing for 16 h, the solid was collected by filtration and then suspended in MeOH (100 mL). Silica gel (10 g) was added and the mixture was evaporated. The dry power was placed on top of a silica gel column (5.5×21 cm) and the column was flash eluted with progressively increasing concentrations of MeOH in CH$_2$Cl$_2$ (%MeOH, vol in L): (0, 1); (1, 1); (2, 1); (3, 1); (5, 2.5). Eluate containing the homogeneous product was evaporated and the solid residue was dried under vacuum at 80° C. for 16 h; 410 mg (1.31 mmol, 60%), mp 171°–174° C. Ir (KBr): ν 3410, 3315, 3215 and 3160 (NH, NH$_2$), 1730 (C=O), and 1680 (C=O, C=N) cm$^{-1}$. Uv, λ $_{max}$ (nm), (ε×10$^{-3}$): pH 1, 302 (9.55), 250 (8.33), 222 (30.3); MeOH, 302 (9.13), 250 (8.64), 220 (29.8); pH 11, 292 (7.73), 250 (7.68), 224 (11.1). $^1$H nmr (DMSO-d$_6$): δ 1.15 (t, 3 H, CH$_3$), 1.47-1.50 (m, 2 H, CH2), 1.61-1.63 (m, 2 H, CH$_2$), 2.32 (t, 2 H, CH$_2$), 3.76 (t, 2 H, NCH$_2$), 4.03 (q, 2 H, OCH$_2$), 6.92 (br s, 2 H, NH$_2$) and 11.1 (br s, 1 H, NH). Anal. Calc'd for C$_{12}$H$_{16}$N$_4$O$_4$S (312.35): C, 46.14; H, 5.16; N, 17.94. Found: C, 46.36; H, 5.06; N, 17.59.

EXAMPLE 15

5-Amino-3-(4-carboxybutyl)thiazolo[4,5-d]-pyrimidine-2,7(3H,6H)-dione

A mixture of 5-amino-3-[4-(ethoxycarbonyl)butyl]-thiazolo[4,5-d]pyrimidine-2,7(3H,6H)-dione (312 mg, 1 mmol) and 1 N NaOH (5 mL) was stirred at ambient temperature for 1.5 h. The mixture was acidified (pH=4) with AcOH and then refrigerated for 16 h. The solid was collected by filtration, crystallized from a MeOH:H$_2$O mixture and dried under vacuum at 80° C. for 16 h; 220 mg (0.774 mmol, 77%), mp 263°–265° C. Ir (KBr): ν 3410, 3315 and 3180 (NH, NH$_2$), 1725 (C=O) and 1640 (C=O), and 1640 (C=O, C=N) cm$^{-3}$. Uv, λ $_{max}$ (nm), (ε×10$^{-3}$): pH 1, 302 (9.79), 250 (8.52), 222 (31.0); MeOH, 302 (9.48), 250 (8.79), 222 (30.40); pH 11, 292 (8.26), 250 (8.15), 224 (12.20). $^1$H nmr (DMSO-d$_6$): δ 1.43-1.50 (m, 2 H, CH$_2$), 1.60-1.67 (m, 2 H, CH$_2$), 2.24 (t, 2 H, CH$_2$), 3.76 (t, 2 H, NCH$_2$), 6.91 (br s, 2 H, NH$_2$) 11.1 (br s, 1 H, NH), and 12.0 (br s, 1 H, COOH) Anal. Calc'd for C$_{10}$H$_{12}$N$_4$O$_4$S (284.30): C, 42.25; H, 4.25; N, 19.71. Found: C, 42.32; H, 4.22; N, 19.69.

EXAMPLE 16

5-Amino-3-(tetrahydrofurfuryl)thiazolo[4,5-d]-pyrimidine-2,7(3H,6H)-dione

A mixture of 5-aminothiazolo[4,5-d]pyrimidine-2,7 (3H,6H)-dione[13] (450 mg, 2.44 mmol), anhydrous DMF (20 mL) and NaH (80% dispersion in mineral oil, 73 mg, 2.47 mmol) was protected from moisture and stirred at ambient temperature for 1 h. Tetrahydrofurfuryl chloride (0.28 mL, 2.57 mmol) was added and the mixture was heated at 140°±3° C. (oil bath) for 1 d. After cooling, the mixture was evaporated in vacuum and then H$_2$O (50 mL) was added. The mixture was stirred for 2 h and then filtered. The flitrate was evaporated and the residue was stirred with MeOH (50 mL). Silica gel (10 g) was added and the mixture was evaporated. The dry powder was placed on top of a silica gel column (5.5×19 cm). The column was flash eluted with progressively increasing concentrations of MeOH in CH$_2$Cl$_2$ (%MeOH, vol in L): (0, 0.5); (1, 0.5); (2, 0.5); (4, 2); (6, 1); (10, 1). Eluate containing the product was evaporated and the solid was dried in vacuum at 80° C. for 2 d; 190 mg (708 μmol, 29%), mp 257°–261° C. (with prior darkening and sintering). A portion (160 mg) of the solid was crystallized from a MeOH:H$_2$O mixture and dried in vacuum at 80° C. for 16 h; 110 mg, mp 266°–68° C. Ir (KBr): ν 3360 and 3110 (NH, NH$_2$), 1710 (C=O) and 1680-1630 broad (C=O, C=N, C=C) cm$^{-1}$. $^1$H nmr (DMSO-d$_6$); δ 1.61-1.66 (m, 1 H, 0.5 CH$_2$), 1.79-1.92 (m, 3 H, 1.5 CH$_2$), 3.59-3.63 (m, 2 H, NCH$_2$), 3.65-3.70 H, 0.5 OCH$_2$), 3.74-3.87 (m, 1 H, 0.5 OCH$_2$), 4.17-4.22 (m, 1 H, OCH), 6.85 (br s, 2 H, NH$_2$), and 11.02 (br s, 1 H, NH). Uv, λ $_{max}$(nm), (ε×10$^{-3}$): pH 1, 302 (9.61), 250 (8.35), 222 (28.5); MeOH, 302 (9.54), 250 (8.80), 222 (28.07); pH 11, 292 (7.81), 250 (7.86), 224 (10.6). Anal. Calc'd for C$_{10}$H$_{12}$N$_4$O$_3$S (268.30): C, 44.77; H, 4.51; N, 20.88. Found: C, 44.86; H, 4.57; N, 20.58.

EXAMPLE 17

5-Amino-3-(4-methyl-3-pentene-1-yl)thiazolo[4,5-d]-pyrimidine-2,7(3H,6H)-dione

A mixture of 5-aminothiazolo[4,5-d]pyrimidine-2, 7 (3H,6H)-dione[13] (440 mg, 2.28 mmol), NaH (80 % dispersion in mineral oil, 75 mg, 2.5 mmol) and anhydrous DMF (20 mL) was protected from moisture and stirred at ambient temperature for 1 h. 5-Bromo-2-methyl-2-pentene (0.35 mL, 2.61 mmol) was added and the mixture was heated at 75°±3° C. (oil bath) for 4 h. After cooling, the mixture was evaporated in vacuum and then H$_2$O (25 mL) was added. The mixture was stirred for 15 min and then the solid was collected by filtration. The solid was stirred with MeOH (50 mL) and the mixture was again filtered. Silica gel (10 g) was added to the MeOH flitrate and the mixture was evaporated. The dry powder was placed on top of a silica gel column (5.5×20 cm) and the column was progressively flash eluted with increasing concentrations of MeOtt in CH$_2$Cl$_2$ (%MeOH, vol in L) : (0, 1); (1, 1); (2, 1); (3, 1); (5, 2)° Eluate containing the homogeneous product was evaporated and the residue was dried in vacuum over P$_2$O$_5$ at 80° C. for 16 h; 390 mg (1.46 mmol, 64 %), mp 240°–242° C. (with prior softening and sintering). Ir (KBr): ν 3430 and 3220 (NH, NH$_2$), 1690 and 1670 (C=O, C=N), and 1650 and 1630 (C=N, C=C) cm$^{-1}$. Uv, λ $_{max}$(nm), (ε×10$^{-3}$): pH 1, 302 (8.52), 248 (7.72), 222 (22.1); MeOH, 304 (8.60), 250 (7.92), 222 (24.2); pH 11, 292 (6.73), 248 (6.77), 226 (11.4). $^1$H nmr (DMSO-d$_6$): δ 1.52 (s, 3 H, CH$_3$), 1.64 (s, 3 H, CH$_3$), 2.30-2.36 (m, 2 H CH$_2$), 3.75 (t, 2 H, NCH$_2$), 5.06-5.10 (m, 1 H, CH), 6.94 (br s, 2 H, NH$_2$), and 11.12 (br s, 1 H, NH$_2$). Anal. Calc'd for C$_{11}$H$_{14}$N$_4$O$_2$S (266.32): C, 49.61; H, 5.30; N, 21.04. Found: C, 49.57; H, 5.30; N, 20.72.

EXAMPLE 18

5-Amino-6-methyl-3-(pent-2-ene-1-yl)thiazolo[4,5-d]-pyrimidine-2,7(3H,6H)-dione

A mixture of 5-amino-3-(pent-2-ene-1-yl)thiazolo[4,5d]-pyrimidine-2,7(3H,6H)-dione (350 mg, 1.35 mmol), NaH (80% dispersion in mineral oil, 42 mg, 1.4 mmol) and anhydrous DMF (15 mL) was protected from moisture and stirred at ambient temperature for 0.25 h. Iodomethane (0.1 mL, 1.61 mmol) was added and the mixture was stirred for an additional 1 h. The mixture was evaporated in vacuum and then H$_2$O (20 mL) was added. The mixture was stirred for 15 min and then the solid was collected by filtration. The solid was suspended in MeOH (25 mL) and silica gel (5 g) was added. The mixture was evaporated and the dry powder was placed on top of a silica gel column (5.5×20 cm). The column was flash eluted with progressively increasing concentrations of MeOH in $CH_2Cl_2$ (%MeOH, vol in L): (0, 1); (1, 1); (2, 1); (3, 1). Eluate containing the homogeneous product was evaporated and the solid was dried in vacuum at 80° C. for 16 h; 240 mg (0.901 mmol, 66%), mp 184°-187° C. Ir (KBr): $\nu$ 3420, 3330 and 3210 ($NH_2$), 1715 (C=O), and 1675 (C=N) cm$^{-1}$. Uv, $\lambda\ _{max}$ (nm), ($\epsilon \times 10^{-3}$): pH 1, 300 (9.37), 252 (8.02), 222 (30.9); MeOH, 302 (9.07), 252 (8.35), 222 (31.3); pH 300 (9.41), 252 (8.08), 226 (21.0). $^1$H nmr (DMSO-$d_6$): $\delta$ 0.954 (t, 3 H, $CH_3$), 2.15-2.22 (m, 2 H, $CH_3CH_2$), 3.29 (s, 3 H, $CH_3$), 4.38 (d, 2 H, $NCH_2$), 5.34-5.40 (m, 1 H, CHCH), 5.53-5.59 (m, 1 H, CHCH), and 7.51 (br s, 2 H, $NH_2$). Anal. Calc'd for $C_{11}H_{14}N_4O_2S$ (266.32): C, 49.61; H, 5.30; N, 21.04. Found: C, 49.93; H, 5.17; N, 20.77.

EXAMPLE 19

5-Amino-2-hexylaminothiazolo[4,5-d]pyrimidine-7(6H)-one

A mixture of 5-amino-2-chlorothiazolo[4,5-d]pyrimidine-7(6H)-one[13] (410 mg, 2.02 mmol), hexylamine (1.3 mL) and $H_2O$ (40 mL) was stirred and heated at reflux for 4.5 h. After cooling to ambient temperature, the solid was collected, washed with $H_2O$ (20 mL) and then washed with acetone (20 mL). The solid was crystalized from a DMF:$H_2O$ mixture and then suspended in a mixture of $H_2O$ (100 mL) and EtOH (100 mL). The mixture was stirred and heated at boiling for 0.25 h. The hot mixture was filtered, the solid was washed with $H_2O$ (25 mL), then acetone (25 mL) and dried at 80° C. in vacuum for 16 h; 410 mg (1.44 mmol, 71%), mp >320° C. Ir (KBr): $\nu$ 3650, 3530, 3460, 3280 and 3130 (NH, $NH_2$), and 1650 broad (C=O, C=N, C=C) cm$^{-1}$. Uv, $\lambda\ _{max}$ (nm), ($\epsilon \times 10^{-3}$): pH 1, 312 (16.5), 260sh (6.81), 228 (26.6); pH 11, 304 (11.3), 236 (33.1). $^1$H nmr (DMSO-$d_6$): $\delta$ 0.870 (t, 3 H, $CH_3$), 1.29-1.36 (m, 8 H, $CH_2$), 6.37 (br s, 2 H, $NH_2$), 8.42 (br s, 1 H, $CH_2N$), and 10.69 (br s, 1 H, NH). Anal. Calc'd for $C_{11}H_{17}N_5OS \cdot H_2O$ (285.37): C, 46.30; H, 6.71; N, 24.54. Found: C, 46.36; H, 6.72; N, 24.57.

EXAMPLE 20

5-Amino-3-(2-deoxy-2-fluoro-3,5-di-O-benzoyl-$\beta$-D-arabino furanosyl)thiazolo[4,5-d]pyrimidine-2,7(3H,6H)-dione To a suspension of 5-aminothiazolo[4,5-d]pyrimidine-2,7(3H, 6H)-dione[13] (2.0 g, 10.86 mmol) in 1,1,1,3,3,3-hexamethyldisilazane (200 mL) was added ($NH_4)_2SO_4$ (0.15 g) and $CH_3CONH_2$ (0.2 g), and the mixture was heated under reflux for 3.5 h under an atmosphere of nitrogen. The clear solution was evaporated in vacuo at 30° C. and the residue was co-evaporated with dry $CHCl_3$ (2×5 mL) to give the trimethylsilyl derivative. The trimethylsilyl derivative was dissolved in dry $CHCl_3$ (95 mL). To this solution was added a solution of 2-deoxy-2-fluoro-3,5-di-O-benzoyl-$\alpha$-D-arabinofuranosyl bromide[32] (4.39 g, 10.86 mmol, obtained from 2-deoxy-2-fluoro-1,3,5-tri-O-benzoyl-$\alpha$-D-arabinofuranose) in $CHCl_3$ (15 mL). The reaction mixture was heated under reflux with stirring for 4 days and evaporated to dryness. The residual syrup was dissolved in $CH_2Cl_2$ (200 mL), washed with saturated solution of $NaHCO_3$ (300 mL), then with NaCl solution (250 mL), dried ($Na_2SO_4$) and evaporated to dryness. The residue was purified on a flash silica gel column using $CH_2Cl_2$:MeOH (93:7, v:v) as the eluent. The appropriate homogeneous fractions were collected and concentrated to give a white foam which on crystallization with aqueous EtOH afforded 0.65 g (41.5%, on the basis of recovered aglycon, 1.45 g) of the title compound as a white crystalline product, mp 282°-284° C. Ir (KBr): $\nu$ 1680 (C=O), 1725 (C=O), and 3340 (NH) cm$^{-1}$. Uv, $\lambda\ _{max}$ (nm), ($\epsilon \times 10^{-3}$): pH 1, 300 (6.2), 234 (18.4), 218 (15.6); pH 7, 302 (7.6), 234 (19.8), 208 (13.6); pH 11, 292 (5.7), 234 (19.4), 214 (15.9). $^1$H nmr (DMSO-$d_6$): $\delta$ 4.51 (q, 1 H, $C_4'H$), 4.54-4.71 (m, 2 H, $C5.CH_2$), 6.07 (tt, $J_{HF}$=46.8 Hz, $C_2'H$), 6.31 (tt, $J_{HF}$=12.8 Hz, 1 H, $C_3'H$), 6.51 (dd, $J_{HF}$=11.6 Hz, $J_{1',2'}$=3.6 Hz, 1 H, $C_1'H$), 7.02 (br s, 2 H, $NH_2$), 7.39-7.72 (m, 6 H, phenyl protons), 8.02 (m, 4 H, orthophenyl protons) and 11.37 (br s, 1 H, NH). Anal. Calc'd for $C_{24}H_{19}FN_4OS_7$: C, 54.75; H, 3.64; N, 10.63; S, 6.08; F, 3.60. Found: C, 54.55; H, 3.62; N, 10.22; S, 5.88; F, 3.61.

EXAMPLE 21

5-Amino-3-(2-deoxy-2-fiuoro-$\beta$-D-arabinofuranosyl)-thiazolo[4,5-d]pyrimidine-2,7(3H,6H)-dione Treatment of 5-amino-3-(2-deoxy-2-fluoro-3,5-di-O-benzoyl-$\beta$-D-arabinofuranosyl)thiazolo[4,5-d]pyrimidine-2,7(3H,6H)-dione (0.40 g, 0.76 mmol) in $NH_3$/MeOH (saturated at 0° C., 35 mL) at room temperature for 24 h gave the deblocked nucleoside. This was dissolved in MeOH, adsorbed on silica gel (10 g) and loaded on the top of a prepacked silica gel column. The column was eluted with $CH_2Cl_2$:MeOH (90:10, v:v). The appropriate fractions were pooled and concentrated to afford 0.21 g (86.9%) of the title compound, mp 232°-234° C.; Ir (KBr): $\nu$ 3200-3450 (OH, NH), 1660 (C=O) and 1677 (C=O) cm$^{-1}$. Uv, $\lambda\ _{max}$ (nm),($\epsilon \times 10^{-3}$): pH 1, 302 (8.4), 242 (8.8), 222 (10.2); pH 7, 302 (8.6), 242 (9.1), 222 (10.3); pH 11, 220 (9.9), 242 (7.6), 294 (6.0); $^1$H nmr (DMSO-$d_6$): $\delta$ 3.65 (t, 2 H, $C_5'H_2$), 4.23 (m, 1 H, $C_4'H$), 4.55 (tt, 1 H, $C_3'H$), 4.72 (m, 1 H, $C_3'OH$), 5.36 (tt, J2,HF=40.4 Hz, 1 H, $C_2'H$), 5.72 (m, 1 H, $C_5'OH$), 6.30 (dd, $J_{1',2'}$=2.12 Hz, 1 $J_{1'H,F}$=12.52 Hz, 1 H, $C_1'H$), 6.96 (br s, 2 H, $NH_2$) and 11.25 (br s, 1 H, NH); Anal. Calc'd for $C_{10}H_{11}OF_5S$ 0.25 $CH_3OH$: C, 37.73; H, 3.71; N, 17.16: S, 9.82; F, 5.82. Found: C, 37.93; H, 3.86; N, 16.72; S, 9.53; F, 5.52.

EXAMPLE 22

5-Amino-2-selenothiazolo[4,5-d]pyrimidine-7(6H)-one

5-Amino-2-chlorothiazolo[4,5-d]pyrimidine-7(6H)-one[13] (13.0 g, 64 mmol) was suspended in absolute ethanol (600 mL) and heated at reflux in the presence of selenourea (8.64 g, 70 mmol) for 30 min, at which time water (5 mL) was added to the hot solution. Refluxing was continued for an additional 30 min. The mixture was then allowed to cool at room temperature and chilled at 4° C. for 16 h. The cold solution was vacuum filtered and the collected material was suspended in boiling water and vacuum filtered (4×250 mL). The collected material was then dried at high vacuum at 90° C. for 20 h, affording 14.05 g (87%) of 5-amino-2-seleno-thiazolo[4,5-d]pyrimidin-7(6H)-one; mp >260° C. $^1$H nmr (DMSO-$d_6$): $\delta$ 6.96 (s, 2 H, $NH_2$) and 11.24 (s 1 H, NH). Ir (KBr): 3340, 3140 (NH, $NH_2$), 975 (C=Se) cm$^{-1}$. Uv, $\lambda_{max}$ (nm) ($\epsilon \times 10^{-3}$): pH 7, 375

(9.07), 285 (7.71); pH 1, 372 (9.53), 284 (7.85), pHH (10.43). Anal. Calc'd for C$_5$H$_4$N$_4$OSSe: C, 24.30; H, 1.63; N, 22.67; S, 12.97; Se, 31.95. Found: C, 22.22; H, 1.53; N, 20.70; S, 12.79; Se, 31.78.

EXAMPLE 23

5-Amino-2-(hexylseleno)thiazolo[4,5-d]pyrimidine-7(6H)-one

5-Amino-2-selenothiazolo[4,5-d]pyrimidine-7(6H)-one (500 mg, 2mmol) was suspended in dry DMF (25 mL) and stirred at room temperature under argon. Sodium hydride (80% dispersion in mineral oil, 105 mg, 2.6 mmol) was added and the mixture was stirred at room temperature for 40 min. 1-Bromohexane was added and the mixture was stirred at room temperature under a dry atmosphere for 20 h. The mixture was evaporated under high vacuum and the remaining residue was suspended in 25 mL of methanol and treated with silica gel (10 g). The mixture was evaporated to dryness and the silica adsorbed material was applied to the top of a silica gel column (5×11 cm) and eluted with hexane (1 L), CH$_2$Cl$_2$ (1 L), 1% MeOH/CH$_2$Cl$_2$ (1 L), 2% MeOH/CH$_2$Cl$_2$ (1 L), 3% MeOH/CH$_2$Cl2 (1 L), 5% MeOH/CH$_2$Cl$_2$ (1 L), and 10% MeOH/CH$_2$Cl$_2$ (4 L). Those fractions having uv-absorbing material with R$_f$=0.47 in 10 % MeOH/CH$_2$Cl$_2$ were pooled and concentrated to dryness; mp>250° C. Ir (KBr): 1090 cm$^{-1}$ (C-Se-C). Anal. Calc'd for C$_{11}$H$_{16}$N$_4$OSSe: C, 39.88; H, 4.87; N, 16.91; S, 9.68. Found: C, 39.82; H, 4.91; N, 16.03; S, 9.60.

EXAMPLE 24

5-Amino-3-(2-pentenyl)-2-selenothiazolo[4,5-d]-pyrimidine-7(6H)-one

A mixture of 5-Amino-2-selenothiazolo[4,5-d]pyrimidine-7(6H)-one (5 g, 20 mmol) was co-evaporated with anhydrous toluene (3×40 mL) and the remaining residue was suspended in anhydrous DMF (250 mL). Sodium hydride (80% dispersion in mineral oil, 890 mg, 22 mmol) was added and the mixture was stirred at room temperature for 1 h while under argon. The mixture was protected from moisture and heated to reflux. Once reflux was achieved, 1-bromo-2-pentene was added and reflux was continued for 16 h. The mixture was allowed to cool to ambient temperature, evaporated to dryness under high vacuum, suspended in methanol (200 mL), adsorbed onto silica gel (80 mL), evaporated to dryness, and applied to the top of a silica gel column (7×15 cm). The column was eluted with CH$_2$Cl$_2$ (1 L), 1% MeOH/CH$_2$Cl$_2$ (1 L), 2% MeOH/CH$_2$Cl$_2$ (1 L), 2.5% MeOH/CH$_2$Cl$_2$ (1 L), 3% MeOH/CH$_2$Cl$_2$ (1 L), 3.5% MeOH/CH$_2$Cl$_2$ (1 L), 4% MeOH/CH$_2$Cl$_2$ (1 L), 4.5% MeOH/CH$_2$Cl$_2$ (1 L), 5% MeOH/CH$_2$Cl$_2$ (1 L), 6% MeOH/CH$_2$Cl$_2$ (1 L), 6.5% MeOH/CH$_2$Cl$_2$ (1 L), 7% MeOH/CH$_2$Cl$_2$ (1 L), 7.5% MeOH/CH$_2$Cl$_{12}$ (1 L). The homogeneous fractions having the appropriate material were pooled and evaporated to dryness to afford 1.06 g (17%) of a yellow material; mp>320° C. $^1$H nmr (DMSO-d$_6$): δ 11.49 (s, 1 H, NH), 7.15 (s, 2 H, NH$_2$), 5.77 (m, 1 H, CH), 5.55 (m, 1 H, CH), 4.87 (d, 2 H, NCH$_2$), 2.03 (m, 2 H, CH$_3$CH$_2$), and 0.94 (t, 3 H, CH$_3$). Ir (KBr): 3280, 3150 (NH, NH$_2$), 1625 (C≡C) and 1010 (C═Se) cm$^{-1}$. Uv, λ$_{max}$ (nm) (ε×10$^{-3}$): pH 1, 370 (17.63), 286 (15.46); pH 7, 376 (20.23), 286 (15.54); pH 11, 368 (16.71), 276 (9.66). Anal. Calc'd for C$_{10}$H$_{12}$N$_4$OSSe: C, 38.10; H, 3.84; N, 17.77; S, 10.17. Found: C, 38.52; H, 3.84; N, 17.49; S, 10.58.

EXAMPLE 25

5-Amino-3-(3-methyl-2-butenyl)-2-selenothiazolo[4,5-d]-pyrimidine-7(6H)-one

A mixture of 5-Amino-2-selenothiazolo[4,5-d]pyrimidine-7(6H)-one (5 g, 20 mmol) was co-evaporated with anhydrous toluene (3×40 mL) and the remaining residue was suspended in anhydrous DMF (250 mL). Sodium hydride (80% dispersion in mineral oil, 890 mg, 22 mmol) was added and the mixture was stirred at room temperature for 1 h while under argon. The mixture was protected from moisture and heated to reflux. Once reflux was achieved, 4-bromo-2-methyl-2-butene (2.63 mL, 22 mmol) was added and reflux was continued for 16 h. The mixture was allowed to cool to ambient temperature, evaporated to dryness under high vacuum, suspended in methanol (200 mL), adsorbed onto silica gel (80 mL), concentrated to dryness, and applied to the top of a silica gel column (7×15 cm). The column was eluted with CH$_2$Cl$_2$ (1 L), 1% MeOH/CH$_2$Cl$_2$ (1 L), 2% MeOH/CH$_2$Cl$_2$ (1 L 2.5% MeOH/CH$_2$Cl$_2$ (1 L), 3% MeOH/CH$_2$Cl$_2$ (1 L), 3.5% MeOH/CH$_2$Cl$_2$ (1 L), 4% MeOH/CH$_2$Cl$_1$ (1 L), 4.5% MeOH/CH$_2$Cl$_2$ (1 L), 5% MeOH/CH$_2$Cl$_2$ (1 L), 6MeOH/CH$_2$Cl$_2$ (1 L), 6.5% MeOH/CH$_2$Cl$_2$ (1 L), 7% MeOH/CH$_2$Cl$_2$ (1 L), 7.5% MeOH/CH$_2$Cl$_2$ (1 L). Those fractions having the appropriate material were pooled and evaporated to dryness to afford 950 mg (15%) of a yellow material; mp>320° C. $^1$H nmr (DMSO-d$_6$): δ 11.47 (s, 1 H, NH), 7.15 (s, 2 H, NH$_2$), 5.25 (m, 1 H, CH), 4.89 (d, 2 H, NCH$_2$), 1.85 (s, 3 H, CH$_3$), and 1.68 (s, 3 H, CH$_3$). Ir (KBr): 3280, 3150 (NH, NH$_2$), 1625 (C═C), and 1010 (C═Se) cm$^{-1}$. Uv, λ$_{max}$ (nm) (ε×10$^{-3}$): pH 1, 370 (17.63), 286 (15.46); pH 7, 376 (20.23), 286 (15.54); pH 11, 368 (16.71), 276 (9.66). Anal. Calc'd for C$_{10}$H$_{12}$N$_4$OSSe: C, 38.10; H, 3.84; N, 17.77. Found: C, 38.93; H, 3.80; N, 17.36.

EXAMPLE 26

5-Amino-3-(β-D-ribofuranosyl)-2-selenothiazolo[4,5-d]-pyrimidin-7(6H)-one

5-Amino-2-selenothiazolo[4,5-d]pyrimidin-7(6H)-one (2.5 g, 10 mmol) was suspended in dry acetonitrile (200 mL) and heated at reflux for 3.5 h in the presence of chlorotrimethylsilane (3 mL, 23.6 mmol), hexamethyldisilazane (5 mL, 23.7 mmol), and trimethylsilyltrifluoromethanesulfonate (TMSOTf, 5 mL, 25.8 mmol). 1-O-Acetyl-2,3,5-tri-O-benzoyl-β-D-ribofuranose (5.1 g, 10.9 mmol) was added as a slurry in acetonitrile (15 mL) and heating was continued for 0.5 h. An aliquot from the reaction mixture failed to give two clear layers upon treatment with aqueous NaHCO$_3$ and ethyl acetate, therefore an additional amount of TMSOTf (3 mL) was added and refluxing was continued for 0.5 h. An aliquot from the reaction mixture was added to aqueous NaHCO$_3$ and treated with ethyl acetate, giving two clear layers. The reaction mixture was poured onto aqueous NaHCO$_3$ (150 mL) and water (2 L) and extracted with ethyl acetate (3×500 mL). The ethyl acetate extracts were dried (Na$_2$SO$_4$) and evaporated to dryness. The remaining residue was suspended in ethyl ether (300 mL), sonicated, and filtered. The collected material was then dried at room temperature under high vacuum for 16 h to yield 6.3 g (91%) of the protected nucleoside. $^1$H nmr (DMSO-d$_6$): δ 11.65 (s, 1 H, NH), 7.98-7.08 (ArH, C$_1$H, NH$_2$), 6.48 (s, 1 H, C$_2$H), 6.35 (t, 1 H, $C_{3'}H$), 4.89 (m, 1 H, $C_{4'}H$), 4.81 (m, 1 H, $C_{5'}H$), and 4.66 (m, 1 H, $C_{5'}H$).

The above protected nucleoside was then deprotected. Thus, 5-amino3-( 2,3,5-tri-O-benzoyl-β-D-ribofuransoyl)-2-selenothiazolo[4,5-d]pyrimidin-7(6H)one (5 g, 7.2 mmol) was suspended in methanol (700 mL) and stirred at room temperature while protected from moisture. Sodium methoxide (1.7 g, 31.5 mmol) was added and stirring was continued for 16 h. Amberlite IR-120 (H+) [20 g, washed with water (6×40 mL) and then with methanol (3×30 mL)] was added and the mixture was stirred for 5 min. The resin was removed by vacuum filtration and repeatedly washed with methanol (100 mL). The methanol flitrate was treated with silica gel (80 mL) and evaporated under reduced pressure. The material adsorbed onto silica gel was applied to a silica gel column (5.5×20 cm). The column was eluted with $CH_2Cl_2$ (1 L), 2% $MeOH:CH_2Cl_2$ (1 L), 5% $MeOH:CH_2Cl_2$ (1 L), 7.5% $MeOH:CH_2Cl_2$ (1 L), 10% $MeOH:CH_2Cl_2$ (3 L), and 15% $MeOH:CH_2Cl_2$ (3 L). Fractions of 200 mL were collected and those having a uv-active material that charred upon treatment with acid and heat were pooled and evaporated to dryness, giving 2.7 g (84%) of the unprotected nucleoside. The isolated material was recrystallized from methanol:water; mp>250° C. (dec.). $^1H$ nmr (DMSO-$d_6$): δ 11.43 (s, 1 H, NH), 6.94 (s, 2 H, $NH_2$), 6.63 (d, 1 H, $C_{3'}H$, J=4.0 Hz), 5.30 (d, 1 H, $C_{2'}OH$, J=5.6 Hz), 4.97 (m, 1 H, $C_{3'}H$), 4.74 (d, 1 H, $C_{3'}OH$, J=6.8 Hz), 4.60 (t, 1 H, $C_{5'}H$), 4.37 (q, 1 H, $C_{2'}H$), 3.78 (m, 1 H, $C_{4'}H$), 3.69 (m, 1 H, $C_{5'}H$), 3.56 (m, 1 H, $C_{5'}H$). Ir (KBr): 3420 (br, NH, $NH_2$), and 1035 (C=Se) cm$^{-1}$. Uv $\lambda_{max}$ (nm) ($\epsilon \times 10^{-3}$): pH 7, 380 (9.587), 300 (shoulder, 3.105), 284 (4.975); pH 1, 376 (9.403), 286 (6.135); pH 11, 375 (8.705), 280 (4.932). Anal. Calc'd for $C_{10}H_{12}N_4O_5SSe\cdot0.5\ H_2O$: C, 30.94; H, 3.37; N, 14.43; S, 8.26. Found: C, 30.78; H, 3.30; N, 14.42; S, 8.68.

EXAMPLE 27

Cells and Viruses

Vero and MRC-5 cells were obtained from ATCC. Human foreskin fibroblast (HFF) and Vero cells were routinely grown in minimal essential medium (MEM) with Earle salts [MEM(E)]supplemented with 10% fetal bovine serum (FBS). MRC-5 cells were grown in Basal Medium Eagle (BME) with 10% FBS and 0.035% $NaHCO_3$. Cells were passaged according to conventional procedures.[33] Human cytomegalovirus (HCMV) strains AD169 and Towne were obtained from the ATCC. Herpes simplex virus type i and type 2 (HSV1 and HSV2) are commercially available.

EXAMPLE 28

Inhibition of HCMV in Culture Using a Cytopathic Effect Assay (CPE)

Two different plaque reduction assays were employed to determine the antiviral efficacy of the test compounds in culture. The first assay used MRC-5 cells and the AD169 strain of HCMV. The second assay used HFF cells and the Towne strain of HCMV. In experiments using MRC-5 cells the growth medium was removed from monolayer cultures in 24-well tissue culture plates. One mL of virus (AD169), diluted in test medium (Dulbecco's modified Eagle medium (DMEM), 2% FBS, 0.1% $NaHCO_3$ and 50 ug gentamicin/mL) was used. The 24-well plates were centrifuged at 2200 rpm for 30 minutes at room temperature to allow the virus to adsorb. Medium was then aspirated from each well of the plates. The individual dilutions of each compound (prepared in test medium) were placed in each test well (0.8 mL/well, 4 wells/dilution). All plates were incubated at 37° C. in a moist atmosphere of 5% $CO_2$. When virus plaques had formed in control cells (HCMV infected, untreated) the medium was aspirated from all wells, and the cells were stained by adding 0.3 mL of 0.2% crystal violet in 10% buffered formalin to each well. After 15 minutes, the stain was removed, cells were rinsed in tap water until the water was clear, and the plates were inverted and dried at room temperature. Plaques were counted by use of a dissecting microscope.

A similar set of experiments designed to monitor HCMV plaque reduction were performed with monolayer cultures of HFF and the Towne strain of HCMV using procedures similar to those reported by Turk et al.[34] Diploid HFF cells were plated 24 hr before use at approximately $1 \times 10^5$ cells/plate. These monolayer cultures were infected with 100 plaque forming units (PFU) of virus. The compounds to be assayed were dissolved in culture medium. Viral adsorption was allowed to proceed for 1 hr at which time virus containing medium was removed and replaced with medium containing the various dilutions of the test compounds. Plaques were counted using crystal violet as described above.

Ganciclovir was used as an anti-HCMV standard in all HCMV assays.

EXAMPLE 29

Inhibition of HSV1 and HSV2 in Culture Using a CPE Assay

Vero cells were plated at $4 \times 10^4$ cells/well in a 96-well microtitre dish in 0.1 mL of MEM(E) with 10% FBS 24 h before infection with virus. The cells were incubated at 37° C. in a 5% $CO_2$ atmosphere. The medium was then removed and 50 μL of media containing 30 to 50 PFU of virus was allowed to adsorb to the cells for 10 minutes at 37° C. The virus containing medium was then removed and the cells were rinsed 3 times with fresh media. A final 100 μL aliquot of fresh medium, containing the various dilutions of test compounds, was then added to each well and the plates were then incubated at 37° C. Plaques were observed 24 hr post-infection and the degree of cytopathic effect scored 40 to 48 h post-infection. Acyclovir was used as a standard in all ttSV assays.

EXAMPLE 30

Cytotoxicity

Stationary uninfected HFF and MRC-5 cells were evaluated for visual cytotoxicity on the scoring basis of 0 (no visual cytotoxicity at 20 fold magnification) to 4 (cell sheet nearly destroyed). Cytotoxicity as measured by inhibition of cell growth was performed in Vero cells using a CellTiter 96 ™ Aqueous Non-Radioactivity Cell Proliferation Assay (Promega). Cytotoxicity assays were performed using a 4 day incubation of test compound with Vero cells plated at 500 cells/well. Each assay was performed in quadruplicate. The resultant data are averaged, graphed and then used to calculate the $TC_{50}$ (median toxic concentration) for the compound tested.

EXAMPLE 31

Results of HCMV Tests

I. A series of guanine analogs containing an alkyl side chain in place of sugar moiety were evaluated for their ability to inhibit HCMV production in acute infection assays in culture and for cytotoxicity in HFF and MRC-5 cells.

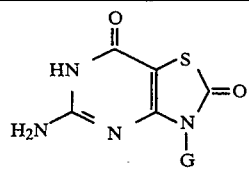

| | |
|---|---|
| R-1132-30 | G = $(CH_2)_5CH_3$ |
| R-1132-36 | G = $(CH_2)_4CH_3$ |
| R-1132-72 | G = $CH_2-CH=CH(CH_3)_2$ |
| R-1132-73 | G = $CH[(CH_2)_3CH_3]_2$ |
| R-1132-74 | G = $CH_2-CH=CH-CH_2CH_3$ |
| R-1132-75 | G = $(CH_2)_3-CH=CH_2$ |
| R-1132-76 | G = $CH(CH_2CH_3)_2$ |
| R-1132-77 | G = $CH[(CH_2)_4CH_3]_2$ |

II. FIG. 4 presents the dose response curve for two of the compounds tested and their antiviral activity relative to ganciclovir.

III. Table 1 lists the median inhibitory concentration ($IC_{50}$) for all compounds tested against HCMV strains AD169 or Towne. In addition this table lists the median toxic concentrations of these compounds ($TC_{50}$) as determined by visual observation of uninfected cells treated with various concentrations of drug.

TABLE 1

Anti-HCMV activity and cytotoxicity of guanine derivatives.

| | Virus and Culture System | | | |
|---|---|---|---|---|
| | AD169/MRC5 | | Towne/HFF | |
| Compound | $IC_{50}$[a] | $TC_{50}$[b] | $IC_{50}$ | $TC_{50}$ |
| R1132-30 | 0.45 | 1.2 | ND[c] | ND |
| R1132-36 | 0.2 | 4.0 | 17 | 100 |
| R1132-72 | 4.0 | >100 | 1.7 | 100 |
| R1132-73 | 9.4 | 178 | 4.7 | 11.1 |
| R1132-74 | <1.0 | >100 | 0.14 | >100 |
| R1132-75 | 9.4 | 68 | 12 | >100 |
| R1132-76 | >100 | 32 | ND | ND |
| R1132-77 | 12 | 52 | ND | ND |
| Ganciclovir | 2.1 | >900 | 2.7 | >100 |

[a]The median inhibitory concentration is presented as µg/mL.
[b]The median toxic concentration (µg/mL) determined by visual observation of the stationary cultures of HFF and MRC-5 cells.
[c]Not determined (ND).

EXAMPLE 32

Results of HSV Tests

I. The same compounds used in Example 31 were also assayed for their ability to inhibit herpes simplex viruses type 1 and type 2 in acute infection assays in culture.

II. A comparison of the antiviral dose response profiles of Rl132-74 and acyclovir is presented in FIG. 5.

III. Table 2 lists the antiviral activity of all compounds tested against HSV1 and HSV2. The toxic effect of these compounds on actively dividing Vero cells is reported. For all values listed as >x, x is the highest concentration tested for the respective compound.

TABLE 2

Anti-Herpes Virus activity and cytotoxicity of guanine derivatives in Vero cells.[a]

| Compound | Cytotoxicity ($TC_{50}$) | HSV1 ($IC_{50}$) | HSV2 ($IC_{50}$) |
|---|---|---|---|
| R1132-30 | >1 | >1.2 | >1.2 |
| R1132-36 | >5 | >5.1 | >5.1 |
| R1132-72 | 20 | 5.6 | 5.6 |
| R1132-73 | >2.5 | >2.2 | >2.2 |
| R1132-74 | >20 | 0.53 | <0.27 |
| R1132-75 | 45 | 16.25 | 8.1 |
| R1132-76 | 56 | >21.7 | 21.7 |
| R1132-78 | >50 | >46.4 | >46.4 |
| acyclovir | >100 | 0.2 | 0.2 |

[a]All toxicity ($TC_{50}$) and inhibitory ($IC_{50}$) values are in µg/mL. All concentrations presented as greater than (>) or less than (<) indicate values greater than or less than the highest or lowest concentration tested.

EXAMPLE 33

Cell Culture Models

I. Inhibition of Acute HIV-1 infections.

Different concentrations of compounds were tested for dose dependent inhibition of syncytium formation in an acute infection assay. Briefly, $HIV_{DV}$ was used to infect the SUP T1 lymphoblastoid cell line using 0.1 tissue culture median infectious doses ($TCID_{50}$) for one hour at 37° C. prior to washing and resuspension in media containing increasing concentrations of the test oligonucleotides. The SUP T1 cells ($2 \times 10^4$ cells/well) were inoculated in triplicate in 200 ul of RPMI 1640 containing 10% fetal calf serum. Four days post-infection the number of syncytium per well were totalled and percent inhibition calculated as compared to untreated control infected cells. Supernatants from wells scored for syncytia formation were also analyzed for the presence of HIV p24 antigert using the standard Coulter p24 antigen capture kit.

II. Inhibition of HCMV in culture using a cytopathic effect assay (CPE).

Plaque reduction assays were employed to determine the antiviral efficacy of the test compounds in culture. MRC-5 cells and the AD169 strain of FICMV were used. Growth medium was removed from monolayer cultures in 24-well tissue culture plates. One ml of virus, diluted in test medium (Dulbecco's modified Eagle medium (DMEM), 2% FBS, 0.1% NaHCO3 and 50 ug gentamicin/ml). After infection and subsequent removal of the media, individual dilutions of each compound (prepared in test medium) were placed in each test well (0.8 ml/well, 4 wells/dilution) and plates incubated at 37° C. in a moist atmosphere of 5% $CO_2$. When virus plaques have formed in control cells (HCMV infected, untreated) the medium was aspirated from all wells, and the cells stained by adding 0.3 ml of 0.2% crystal violate in 10% buffered formalin to each well. Plaques were counted by use of a dissecting microscope. Ganciclovir was used as an anti-HCMV standard in all HCMV assays.

III. Inhibition of HSV1 and HSV2 in culture using a CPE assay.

Vero cells were plated in a 96-well microtitre dish in 0.1 ml of MEM(E) with 10% FBS 24 hours before infection with virus. The medium will then be removed and 50 ul of media containing 30 to 50 PFU of virus were allowed to adsorb to the cells for 10 minutes at 37° C. The virus-containing medium will then be removed and the cells rinsed 3 times with fresh media. A final 100 ul aliquot of fresh medium, containing the various dilutions of test compounds, were added to each well and the plates incubated at 37° C. Plaques were observed 24 hours post-infection and the degree of cytopathic effect scored 40 to 48 hours-post infection. Acyclovir was used as a standard in all HSV assays.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

One skilled in the art would readily appreciate that the present invention is well adapted to carry out the objects and obtain the ends and advantages mentioned as well as those inherent therein. The compounds, compositions and combinations with the methods, procedures and treatments described herein are presently representative of the preferred embodiments, are exemplary and are not intended as limitations on the scope of the invention. Changes therein and other uses will occur to those skilled in the art which are encompassed within the spirit of the invention or are defined by the scope of the claims.

What we claim is:

1. A compound for treating a pathophysiological state caused by a virus which is:
   an antiviral guanine analog having the structure

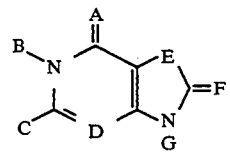

wherein A is O, B is H, C is $NH_2$, D is N, E is S, F is O, and G is $-CH_2CH=CH-CH_2CH_3$ (cis & trans), and pharmaceutically acceptable salts thereof.

2. A composition for treating viral infection in an animal comprising an effective amount of the compound from claim 1 admixed with a physiological carrier.

3. A composition for treating viral infection in an animal [comprised of]comprising:
   an effective amount of a first therapeutic compound from claim 1;
   an effective amount of a second therapeutic compound; and
   said first and second therapeutic compounds admixed in a physiological carrier.

4. The composition of claim 3, wherein the second therapeutic compound is selected from the group consisting of acyclovir, 9-(4-hydroxybutyl)guanine (HBG) and ganciclovir.

* * * * *